(12) United States Patent
Hayashida

(10) Patent No.: US 7,749,707 B2
(45) Date of Patent: Jul. 6, 2010

(54) METHOD FOR OBTAINING SUBTRACTION POLYNUCLEOTIDE

(75) Inventor: Yukinobu Hayashida, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 316 days.

(21) Appl. No.: 11/816,652

(22) PCT Filed: Feb. 27, 2006

(86) PCT No.: PCT/JP2006/303585

§ 371 (c)(1), (2), (4) Date: Aug. 20, 2007

(87) PCT Pub. No.: WO2006/093082

PCT Pub. Date: Sep. 8, 2006

(65) Prior Publication Data
US 2009/0053698 A1 Feb. 26, 2009

(30) Foreign Application Priority Data
Mar. 1, 2005 (JP) ............................. 2005-055279

(51) Int. Cl.
C12Q 1/68 (2006.01)
C12P 19/34 (2006.01)
C07H 21/00 (2006.01)
C07H 21/02 (2006.01)
C07H 21/04 (2006.01)

(52) U.S. Cl. .................... 435/6; 435/91.2; 536/22.1; 536/23.1; 536/24.3

(58) Field of Classification Search .................. 435/6, 435/91.2; 536/22.1, 23.1, 24.3
See application file for complete search history.

(56) References Cited

U.S. PATENT DOCUMENTS 5,525,471 A * 6/1996 Zeng .............................. 435/6
6,235,503 B1 * 5/2001 Lindemann et al. ........ 435/91.2
6,455,255 B1 * 9/2002 Birkenmeyer et al. .......... 435/6
2002/0106666 A1 8/2002 Hayashizaki

FOREIGN PATENT DOCUMENTS

| JP | 2001-269172 A | 10/2001 |
| JP | 2002-253237 A | 9/2002 |
| JP | 2005-218385 A | 8/2005 |
| WO | WO 95/11986 A1 | 5/1995 |
| WO | WO 03/048378 A2 | 6/2003 |
| WO | WO 03/102243 A1 | 12/2003 |
| WO | WO 2005/075643 A1 | 8/2005 |

OTHER PUBLICATIONS

Saiki et al., Genetic analysis of amplified DNA with immobilized sequence-specific oligonucleotide probes. PNAS 86(16) : 6230-6234 (1989).*
Coche et al., *Nucleic Acids Research*, 22(21): 4545-4546 (1994).
Duguid et al., *Nucleic Acids Research*, 18(9): 2789-2792 (1990).
Hara et al., *Nucleic Acids Research*, 19(25): 7097-7104 (1991).
Hayashida, Wako Junyaku Jiho, Technical Report, 73(3): 5-7 (Jul. 15, 2005) Int. Search Report.
Hayashida, 28$^{th}$ Annual Mtg. of the Mol. Bio. Scienty of JP, 758, 3p-1162 (Nov. 25, 2005) Int. Search Report.
Hedrick et al., Nature, 308: 149-153 (1984).
Higuchi et al., *Nucleic Acids Research*, 17(14): 5865 (1989).
Moll et al., *J. Steroid Biochem. & Mol. Bio.*, 89-90: 261-267 (2004).
Zhulidov et al., *Nucleic Acids Research*, 32(3): e37 (2004).

* cited by examiner

*Primary Examiner*—Ethan Whisenant
(74) *Attorney, Agent, or Firm*—Leydig, Voit & Mayer, Ltd.

(57) ABSTRACT

The present invention provides a method for obtaining or amplifying a polynucleotide (a tester-specific polynucleotide), in which an amount existing in a sample (tester) is larger than the amount existing in another sample (driver), easily and within a short time as well as with high efficiency, a polynucleotide obtained (amplified) by such method, a method for identifying gene mutation in the tester, and a kit to be used in such methods.

13 Claims, 8 Drawing Sheets

Preparation of single-stranded tester cDNA

PCR amplification of single side alone with 5'-terminal phosphorylated primer from cDNA library

Removal of hybridized double-stranded cDNA (Step (2))

Removal of hybridized double-stranded cDNA by double-strand specific DNA nuclease treatment

Fig. 6

Amplification of non-hybridized single-stranded tester-specific cDNA (Step (3))

PCR amplification of non-hybridized tester cDNA by primer used in tester cDNA preparation

 (tester-specific polynucleotide)

 (tester-specific polynucleotide)

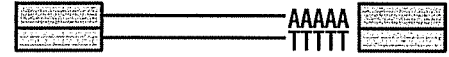 (tester-specific polynucleotide)

5' ——————AAAAA 3'  (driver-non-specific polynucleotide)

3' ——————TTTTT 5'  (driver-non-specific polynucleotide)

5' ——————AAAAA 3'  (driver-specific polynucleotide)

3' ——————TTTTT 5'  (driver-specific polynucleotide)

Removal of non-hybridized single-stranded driver cDNA (Step (4))

SEQUENCE LISTING

<160> NUMBER OF SEQ ID NOS: 7

<210> SEQ ID NO 1
<211> LENGTH: 37
<212> TYPE: DNA
<213> ORGANISM: Artificial
<220> FEATURE:
<223> OTHER INFORMATION: Oligonucleotide primer -continued

```
<400> SEQUENCE: 1 ttttttttaat taatttttt tttttttttt ttttttt                              37

<210> SEQ ID NO 2
<211> LENGTH: 22
<212> TYPE: DNA
<213> ORGANISM: Artificial
<220> FEATURE:
<223> OTHER INFORMATION: Oligonucleotide primer

<400> SEQUENCE: 2
ccagtcacga cgttgtaaaa cg                                              22

<210> SEQ ID NO 3
<211> LENGTH: 22
<212> TYPE: DNA
<213> ORGANISM: Artificial
<220> FEATURE:
<223> OTHER INFORMATION: Oligonucleotide primer

<400> SEQUENCE: 3
cacacaggaa acagctatga cc                                              22

<210> SEQ ID NO 4
<211> LENGTH: 22
<212> TYPE: DNA
<213> ORGANISM: Artificial
<220> FEATURE:
<223> OTHER INFORMATION: Oligonucleotide primer

<400> SEQUENCE: 4
gagtacgtcg tggagtccac tg                                              22

<210> SEQ ID NO 5
<211> LENGTH: 21
<212> TYPE: DNA
<213> ORGANISM: Artificial
<220> FEATURE:
<223> OTHER INFORMATION: Oligonucleotide primer

<400> SEQUENCE: 5
gtacggacat tcagactgct g                                               21

<210> SEQ ID NO 6
<211> LENGTH: 21
<212> TYPE: DNA
<213> ORGANISM: Artificial
<220> FEATURE:
<223> OTHER INFORMATION: Oligonucleotide primer

<400> SEQUENCE: 6
cctcacagtt gccatgtaga c                                               21

<210> SEQ ID NO 7
<211> LENGTH: 22
<212> TYPE: DNA
<213> ORGANISM: Artificial
<220> FEATURE:
<223> OTHER INFORMATION: Oligonucleotide primer

<400> SEQUENCE: 7
catccaggag agccaagcat tg                                              22
```

METHOD FOR OBTAINING SUBTRACTION POLYNUCLEOTIDE

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,495 bytes ASCII (Text) file named "SequenceListing.txt," created Aug. 10, 2007.

TECHNICAL FIELD

The present invention relates to a method for obtaining or amplifying a polynucleotide, in which an amount existing in a sample (tester) is larger than the amount existing in another sample (driver).

BACKGROUND ART

In cells or tissues different in their functions or properties, genes with different expression level exist, and there is a possibility that they play important role in the functional analysis of cells or tissues. It is useful to obtain such genes for elucidation of their functions and expression mechanisms.

On the other hand, a method for cloning genes with different expression levels between cells or tissues with different functions or properties is known as cDNA subtraction method.

The cDNA subtraction method is performed by the following procedures.

For example, in case of analyzing specific function and properties of cancer cell tissues:

(1) At first, a single-stranded RNA or cDNA (tester) prepared from cancer cell tissues and excess amount of single-stranded RNA or cDNA prepared from normal cell tissues, or double-stranded cDNA (driver) are subjected to hybridization. At this time, the gene expressing both Tester and Driver together (housekeeping gene, etc.) forms double-stranded cDNA or RNA-DNA hybrid, however, RNA or cDNA derived from gene specifically expressing in Tester does not form hybrid, and is remained in a state of single-stranded RNA or cDNA.

(2) Subsequently, the single-stranded RNA or cDNA derived from gene, which is specifically expressed in tester and does not form hybrid, is separated from the hybridized double-stranded cDNA or RNA-DNA hybrid to concentrate the genes which is tester-specifically expressed, for example, by the hydroxyapatite chromatography (Hendrick, S. M., Cohen, D. I., Nielsen, E. L. and Davis, M. M. (1984) Nature. 308, 149-153), Avidin-Biotin binding method (Duguin, J. R. and Dinauer, M. C. (1990) Nucleic Acid Research. 18, 2789-2792, JP-A-9-507021), oligo $(dT)_{30}$ solid phase method (Hara, E., Kato T., Nakada, S., Sekiya, L. and Oda, K., (1991) Nucleic Acid Research. 19, 7097-7104 JP-A-2001-269172), Avidin-Biotin-Magnetic Beads method (JP-A-2001-269172 and JP-A-2002-253237), and the like.

However, since the above methods utilized physical binding or adsorption, and separated the single-stranded RNA or cDNA derived from tester-specifically expressing gene and the hybridized double-stranded cDNA or the RNA-DNA hybrid, these materials could not be properly separated, and there was a problem that admixing the hybridized double-stranded cDNA or RNA-DNA hybrid might be admixed. As a result, in the above methods, frequent contamination of the expressed genes in tester and driver (for example, housekeeping gene) might occur, consequently the tester-specific expressing genes could not be concentrated (obtained) efficiently. In addition, the above methods are complicated in operation with a large number of working steps, consequently there was a problem that time and skill are required.

DISCLOSURE OF THE INVENTION

Problem to be Solved by the Invention

The present invention provides a method for obtaining or amplifying a polynucleotide, in which an amount existing in a sample (tester) is larger than the amount existing in another sample (driver), easily and within a short time as well as with high efficiency, a polynucleotide obtained (amplified) by such method, a method for identifying gene mutation in the tester, and a kit to be used in such methods.

Means for Solving Problem

The present invention comprises following constitutions.

1. A method for obtaining a polynucleotide, in which an amount existing in a sample (tester) is larger than the amount existing in another sample (driver) comprising the following steps:

(1) forming a double-stranded polynucleotide consisting of a single-stranded polynucleotide derived from the tester and a single-stranded polynucleotide derived from the driver, which is a complementary strand with the single-stranded polynucleotide derived from the tester, by (i) performing hybridization with the single-stranded polynucleotide derived from the tester and the single-stranded polynucleotide derived from the driver, which can be the complementary strand with the single-stranded polynucleotide derived from the tester, or (ii) performing hybridization after mixing the single-stranded polynucleotide derived from the tester and the double-stranded polynucleotide derived from the driver and subjecting to thermal denaturation; and (2) removing the hybridized double-stranded polynucleotide by enzymatic treatment.

2. A method for amplifying a polynucleotide, in which an amount existing in a sample (tester) is larger than the amount existing in another sample (driver) comprising the following steps:

(1) forming a double-stranded polynucleotide consisting of a single-stranded polynucleotide derived from the tester and a single-stranded polynucleotide derived from the driver, which is a complementary strand with the single-stranded polynucleotide derived from the tester, by (i) performing hybridization after mixing the single-stranded polynucleotide derived from the tester and the single-stranded polynucleotide derived from the driver, which can be the complementary strand with the single-stranded polynucleotide derived from the tester, or (ii) performing hybridization after mixing the single-stranded polynucleotide derived from the tester and the double-stranded polynucleotide derived from the driver and subjecting to thermal denaturation;

(2) removing the hybridized double-stranded polynucleotide by enzymatic treatment; and (3) amplifying the non-hybridized single-stranded polynucleotide derived from the tester.

3. A method for identifying gene mutation in the tester comprising identifying the polynucleotide (existing specifically in tester) obtained by the above method 1, or the polynucleotide (existing specifically in tester) amplified by the above method 2.

4. A polynucleotide (existing specifically in tester) obtained by the above method 1, or amplified by the above method 2.

5. A kit for obtaining or amplifying the polynucleotide (existing specifically in tester) comprising the double-strand specific DNA nuclease and the enzyme for converting the polynucleotide derived from the tester to the single-stranded polynucleotide.

Namely, the present inventors have studied extensively away to attain the above objects, and found that a polynucleotide, in which an amount existing in the tester is larger than the amount existing in the driver, can be obtained or amplified easily, within a short time and with high efficiency, by removing the double-stranded polynucleotide constructed by the subtractive hybridization of the single-stranded polynucleotide derived from the tester and the single-stranded polynucleotide derived from the driver, which is a complementary strand with the single-stranded polynucleotide derived from the tester by means of enzymatic treatment, and completed the present invention.

Effect of the Invention

According to the method of the present invention, the polynucleotide, in which an amount existing in the tester is larger than the amount existing in the driver, can be obtained or amplified easily, within a short time and with high efficiency, and as a result, gene mutation in the tester can be identified with a high degree of accuracy.

BRIEF DESCRIPTION OF DRAWINGS

FIG. 6 is a schematic drawing of the amplification step [step (3)] of non-hybridized single-stranded tester specific cDNA of the present invention.

BEST MODE FOR CARRYING OUT THE INVENTION

1. Sample

Figure 1:
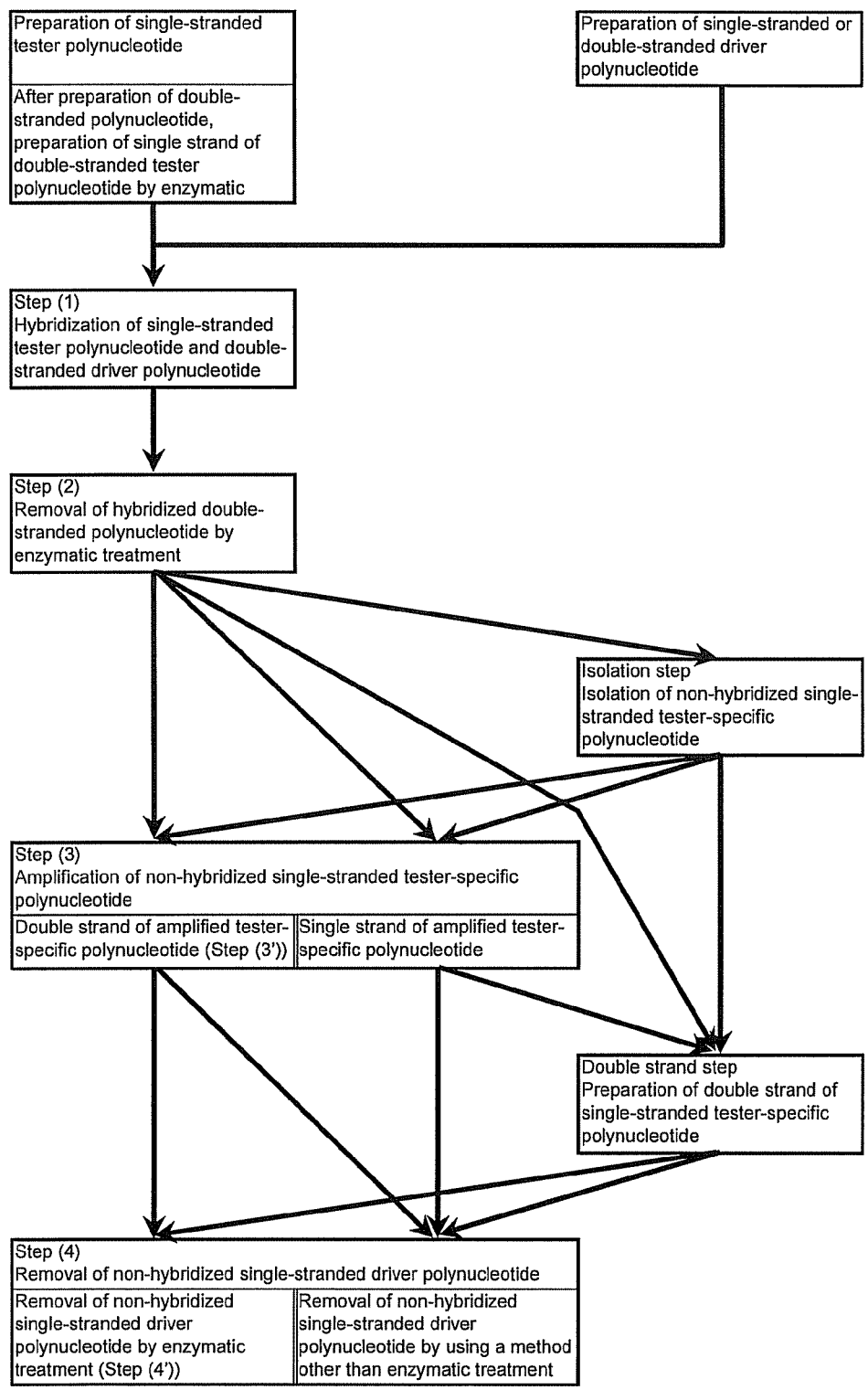
FIG. 1 is a chart showing the method for obtaining or amplifying the polynucleotide of the present invention.

In the present invention, "a sample (tester)" and "another sample (driver)" have the meaning that both are different from each other including, for example, (1) a case when types of the samples are different, but origins of the samples (living organism (individual, population), places, and the like) are identical; (2) a case when types of the samples are identical, but origins of the samples are different; (3) a case when types of the samples and origins of the samples are different; and (4) a case when types of the samples and origins of the samples are identical.

More specifically, they includes, for example, (1) different types of cells, tissues, organs, body fluid, etc. in the same individual (living organism), (2) identical type of cells, tissues, organs, body fluid, etc. between the different individuals (living organism, goods) (between the specific individual and the standard (normal) individual), or between the specific individual (living organism, goods) and the population (between the specific individual and the standard (normal) population), (3) different types of cells, tissues, organs, body fluid (abnormal cells and normal cells, abnormal tissues and normal tissues, abnormal organs and normal organs, abnormal body fluid and normal body fluid, etc.) between different individuals (between diseased individual and standard (normal) individual), or between specific individual and population (between diseased individual and standard (normal) population), and (4) identical type of cells, tissues, organs, body fluid, etc. in the identical individual (living organism) in the case of different environments, conditions, etc (pre- and post-administration of drug, before and after addition of stress, different stage of disease, etc.).

Type of samples to which the present invention is applied is not particularly limited, so long as the type is used in this field. Examples of such samples are, for example: samples derived from living organism such as cells, tissues, organs, body fluid (blood, serum, plasma, spinal fluid, synovial fluid, pancreatic fluid, lymph fluid, etc.), excretory substance (urine, saliva, feces, etc.), sputum, pus, material derived from skin, etc.; microorganisms (fungi, bacteria, virus, etc.); for example environmental samples (foods, beverages, tap water, sea water, lake water, river water, industrial waste, semiconductor washing water, washing fluid after washing medical appliances, etc.); extract obtained therefrom; and treated matters obtained from reconstruction with properly dissolving these samples in water or conventionally used buffers (Tris-buffer, glycine buffer, phosphate buffer, veronal buffer, borate buffer, Good's buffer, etc.) in this field.

In the present invention, the term, "an amount existing in a sample (tester) is larger than the amount existing in another sample (driver)" means (1) a case when a polynucleotide is existing in the tester, but not existing in the driver, and (2) a case when a polynucleotide is existing in both of the tester and the driver, but an amount existing in the tester is comparatively larger than the amount existing in the driver. In addition, "existing specifically in the tester" and "tester-specific" are the same meaning.

"Polynucleotide" obtained and amplified by the method of the present invention (i.e. a polynucleotide in which an amount existing in a sample (tester) is larger than the amount existing in another sample (driver)) includes, for example, RNA such as mRNA, and DNA such as cDNA derived from the mRNA and genomic DNA. Among them, the method of the present invention is effective for obtaining and amplifying DNA such as cDNA derived from mRNA and genomic DNA, and is extremely effective for obtaining and amplifying cDNA derived from mRNA, in which an amount existing in the tester is larger than the amount existing in the driver.

2. Method of the Present Invention

The present invention relates to a method for obtaining or amplifying a polynucleotide, in which an amount existing in a sample (tester) is larger than the amount existing in another sample (driver) (hereinafter, abbreviated as tester-specific polynucleotide).

The method for obtaining the nucleotide of the present invention is characterized by (1) forming a double-stranded polynucleotide consisting of a single-stranded polynucleotide derived from the tester and a single-stranded polynucleotide derived from the driver, which is a complementary strand with the single-stranded polynucleotide derived from the tester, by performing hybridization using the single-stranded polynucleotide derived from the tester with the single-stranded or the double-stranded polynucleotide derived from the driver, and (2) removing the hybridized double-stranded polynucleotide by enzymatic treatment.

Further, a large amount of polynucleotide, in which an amount existing in the tester is larger than the amount existing in the driver can be obtained by amplifying the non-hybridized single-stranded polynucleotide derived from the tester after removing the double-stranded polynucleotide.

Namely, the method for amplifying the nucleotide of the present invention is characterized by (1) forming a double-stranded polynucleotide consisting of a single-stranded polynucleotide derived from the tester and a single-stranded polynucleotide derived from the driver, which is a complementary strand with the single-stranded polynucleotide derived from the tester, by performing hybridization using the single-stranded polynucleotide derived from the tester with the single-stranded or the double-stranded polynucleotide derived from the driver; (2) removing the hybridized double-stranded polynucleotide by enzymatic treatment; and (3) amplifying the non-hybridized single-stranded polynucleotide derived from the tester.

2-1. Method for Obtaining Tester-Specific Polynucleotide of the Present Invention (1) A Single-Stranded Polynucleotide Derived from Tester A polynucleotide derived from the tester of the present invention (hereinafter designates as tester polynucleotide) is a single-stranded polynucleotide. The single-stranded polynucleotide may be DNA or RNA, preferably DNA. Among them, the genomic DNA and the cDNA derived from mRNA existing in the tester (that is cDNA synthesized by mRNA as a template extracted from the tester), specifically preferably cDNA.

The single-stranded tester polynucleotide of the present invention can be prepared appropriately from the above-described samples. Preparation of the single-stranded polynucleotide can be performed by selecting as appropriate from the known methods conventionally used in this field, and commercially available kit can also be used.

Such method is not particularly limited so long as the method is used conventionally in this field. For example, the method for preparing single-stranded polynucleotide directly from the previously described sample (e.g. Vieira J, Messing J. Methods in Enzymology. 1987; 153:3-11; Krieg P A, Melton D A. Methods in Enzymology. 1987; 155:397-415; Davanloo P, Rosenberg A H, Dunn J J, Studier F W. Proc. Natl. Acad. Sci. USA., 1984 April; 81(7):2035-9, and others), the method for preparing single-stranded polynucleotide from double-stranded polynucleotide after preparing the double-stranded polynucleotide from the previously described sample (e.g. Higuchi R G, Ochman H. Nucleic Acid Research. 1989, Jul. 25; 17(14):5865; Guo L H, Wu R., Methods in Enzymology. 1983; 100:60-96, and others), and such method that PCR amplification is performed by using primer labeled with biotin in one side of the PCR primer, and amplified product is mixed with magnetic streptavidin beads to recover the single-stranded DNA, can be used. Further, commercially available kit can also be used. Preparation of the Double-Stranded Polynucleotide can Also be employed by appropriately selecting known methods used conventionally in this field (e.g. Kazuo Maruyama and Sumio Sugano, Gene, 138 (1994) 171-174; Diatchenko, L., et al. Proc. Natl. Acad. Sci. USA 91:6025-6030 (1996); Notomi T, Okayama H, Masubuchi H, Yonekawa T, Watanabe K, Amino N, Hase T. Nucleic Acids Res. 2000 Jun. 15; 28 (12):E63; and Shimada M, Hino F, Sagawa H, Mukai H, Asada K, Kato I. Rinsho Byori. 2002 May; 50(5):528-32). Commercially available kits can also be used.

Further, in the above description, single-stranded polynucleotide and double-stranded polynucleotide to be prepared may be a polynucleotide existing in the tester, or a polynucleotide, which is amplified from the polynucleotide existing in the tester as a template by the known amplification method such as polymerase chain reaction (PCR) and is complementary and/or homologous to the polynucleotide existing in the tester.

In the present invention, among the methods for obtaining the single-stranded tester nucleotide as described hereinabove, the method for preparing the single-stranded polynucleotide by enzymatic treatment after preparing double-stranded polynucleotide (e.g. Higuchi R G, Ochman H. Nucleic Acid Research. 1989 Jul. 25; 17(14): 5865 and Guo L H, Wu R. Methods in Enzymology. 1983; 100:60-96) is preferable, and in particular, the method for preparing a single-stranded polynucleotide by enzymatic treatment after amplifying the polynucleotide complementary and/or the homologous to the polynucleotide existing in the tester by the known amplification method such as PCR using the polynucleotide as a template existing in the tester (e.g. Higuchi R G, Ochman H. Nucleic Acid Research. 1989 Jul. 25; 17(14): 5865) is preferable.

Consequently, the method for obtaining the single-stranded tester nucleotide of the present invention is preferably the method comprising (1') the step for preparing the single-stranded polynucleotide by enzymatic treatment of the double-stranded polynucleotide derived from the tester after preparing the double-stranded polynucleotide derived from the tester, and in particular, the method is preferably the method comprising (1") the step for preparing the single-stranded polynucleotide by enzymatic treatment of the amplified double-stranded polynucleotide derived from the tester after amplifying the double-stranded polynucleotide derived from the tester.

Further, in the above-described method, examples of the enzyme to be used in the enzymatic treatment is not particularly limited so long as the enzyme is those conventionally used in this field, and include, for example, an enzyme having property to prepare a single-stranded polynucleotide by removing single-sided nucleic acid chain of the double-stranded polynucleotide such as lambda exonuclease, and for example, an enzyme which can prepare a single-stranded polynucleotide by removing single-sided nucleic acid chain of the double-stranded polynucleotide by combining two or more enzymes (for example, combination of a restriction enzyme which can generate 5'-protruding end, a restriction enzyme which can generate 3'-recessive end, and an enzyme having 3'→5' endonuclease activity which recognizes 5'-protruding end such as exonuclease III, etc.). Origin of these enzymes is not particularly limited, and any of the enzymes obtainable by the known method and commercially available enzymes can be used.

In addition, reagents and reaction conditions to be used in the above methods may be those according to the known methods.

Amount of nuclease is not particularly limited so long as the amount is sufficient to prepare the single-stranded polynucleotide by sufficiently decomposing the single-sided chain of the double-stranded polynucleotide. Specifically, although it cannot be categorically the because it depends on types of nuclease to be used, however, for example, when lambda exonuclease is used as the enzyme, the amount is generally 0.1 unit to 100 units, preferably 0.5 unit to 50 units, and more preferably 1 unit to 10 units for DNA 2 µg.

Conditions of the enzyme treatment (temperature, time, pH, etc.), specifically conditions of the reaction (contact) of the double-stranded polynucleotide with lambda exonuclease, are generally at 25° C. to 60° C., preferably at 30° C. to 50° C., more preferably at 35° C. to 40° C., and generally at pH 7 to 11, preferably at pH 8 to 10.5, more preferably at pH 9 to 10, for generally 0.1 min. to 60 min., preferably 0.5 min. to 45 min., more preferably 1 min. to 30 min.

Further, in order to maintain the above pH range, buffers generally used in this field can be used. Such buffer is not particularly limited so long as the buffer has buffering capacity in the pH range described above, and includes, for example Tris-HCl buffer, glycine buffer and Good's buffer (e.g. HEPES, PIPES, etc.). Concentration to be used may be in the range of concentration generally used in this field, and selected as appropriate, for example, from a range of generally 1 mM to 500 mM, preferably 5 mM to 250 mM, and more preferably 10 mM to 100 mm.

In this connection, after performing the enzyme treatment as described above, termination of the enzyme reaction is performed, for example, by a method using a reaction terminator, for example, chelating agents such as EDTA, and the like, and/or a method employing heat treatment.

The method using a reaction terminator is such way that, for example, the reaction terminator is contained in water or in the buffer as described hereinabove, and the solution containing the reaction terminator and the reaction solution obtained by performing enzyme treatment are admixed, to make the reaction terminator exist in the reaction solution obtained by the enzyme treatment.

The method for terminating the reaction by heating may be performed by treating the reaction solution obtained by the enzyme treatment generally at 60° C. to 95° C., preferably 70° C. to 90° C., and more preferably 80° C. to 85° C.

Reaction time of the method using a reaction terminator and heat treatment time are generally 5 min. to 60 min., preferably 10 min. to 30 min., and more preferably 15 min. to 20 min.

Among the above reaction terminating methods, a combination of the method using a reaction terminator and the method using heat treatment is preferable.

In this connection, when the double-stranded polynucleotide is reacted with the lambda exonuclease, an activator (e.g. metal ion such as magnesium ion derived from magnesium salt such as magnesium chloride, magnesium sulfate and the like), a surfactant (e.g. Triton-X100 (polyoxyethylene (10) octylphenyl ether), and the like), a stabilizer (thiol compound such as dithiothreitol, mercapto ethanol, and the like), an antiseptics, and the like, which are generally used in this field, may be present. In particular, coexistence of a magnesium salt and a surfactant is preferable. Further, amounts of these substances to be used can be selected, as appropriate, from a range used in this field, and specifically, use amount of magnesium salt is generally 0.1 mM to 100 mM, preferably 0.5 mM to 50 mM, and more preferably 1 mM to 10 mM, and use amount of surface active agent is generally 0.001 to 1% (w/v), preferably 0.005 to 0.5% (w/v), and more preferably 0.01 to 0.1% (w/v).

Further, the single-stranded tester polynucleotide used in the present invention is preferably a polynucleotide bound (added) with an adaptor comprising known sequence at the 5'-terminal and/or 3'-terminal, in particular, the adapter is preferably bound (added) at both terminals of 5'-terminal and 3'-terminal. The adaptor may contain any sequence, and number of bases thereof is preferably such degree that the adapter can function by itself as a primer. Consequently, base number of the adaptor is generally 15 bp to 60 bp, preferably 20 bp to 35 bp, and more preferably 25 bp to 30 bp.

In this connection, when adaptors are bound (added) to both terminals of 5'-terminal and 3'-terminal, if the adaptors of both terminals are complementary, the adapters could form an adaptor hybrid within the single-stranded tester polynucleotide. Therefore, it is preferable to bind non-complementary adaptors in both terminals. Further, the adaptor preferably consists of the sequence which does not exist in the polynucleotide derived from the driver.

In such way, by binding (adding) the adapter described above to the single-stranded tester polynucleotide, the polynucleotide obtained by the method for obtaining the tester-specific polynucleotide of the present invention can be readily isolated and purified from the (single-stranded) polynucleotide derived from the driver.

Further, the adaptor as described above is useful in amplifying the polynucleotide obtained by the method for obtaining the tester-specific polynucleotide of the present invention (the single-stranded polynucleotide derived from non-hybridized tester) in the method for amplifying polynucleotide of the present invention described below. Namely, by preparing the adaptor having the known sequence, in which the primer for amplification reaction such as PCR performed in the step (3) described later is bound, the tester-specific polynucleotide can be readily amplified by using the primer, which is bound with the adaptor.

Method for binding (adding) the adaptor to the single-stranded tester polynucleotide can be selected, as appropriate, from the known methods generally used in this field, and commercially available kits can also be used.

Such method is not particularly limited so long as the method is used generally in this field, and includes: (1) a method of binding (adding) the adaptor with the single-stranded polynucleotide prepared by the method described hereinabove (e.g. oligo-capping method described in "Oligo-capping: a simple method to replace the cap structure of eukaryotic mRNAs with oligoribonucleotides", Kazuo Maruyama and Sumio Sugano. Gene, 138 (1994) 171-17; SMART method described in Diatchenko, L., et al. Proc. Natl. Acad. Sci. USA 91:6025-6030 (1996); Gene Trapper method described in "High-efficiency full-length cDNA cloning by biotinylated CAP trapper", Carninci P, Kvam C, Kitamura A, Ohsumi T, Okazaki Y, Itoh M, Kamiya M, Shibata K, Sasaki N, Izawa M, Muramatsu M, Hayashizaki Y, Schneider C, Genomics. 1996 Nov. 1; 37(3): 327-36, etc.; (2) a method, in which, in the method described above, after binding (adding) the adaptor to the double-stranded polynucleotide prepared, a single-stranded polynucleotide is prepared from the double-stranded polynucleotide (e.g. PACE method described in "Determination of 5' ends of specific mRNAs by DNA ligase-dependent amplifyication", Bertling W M, Beier F. Reichenberger E., PCR Methods Appl. 1993 October; 3(29: 95-9, etc.); and (3) a method, in which, in the above method, a complementary and/or a homologous polynucleotide to the polynucleotide, to which the adapter (primer) is bound (added), is amplified by known amplification method such as PCR method, LAMP method, ICAN method, etc. using the primer designed based on the adaptor sequence, as a template using polynucleotide existing in the tester.

In the above method (3), when the amplified polynucleotide is double-stranded polynucleotide, the double-stranded polynucleotide is required to be converted into the single-stranded polynucleotide according to the method described hereinabove. In such case, by phosphorylating the one-sided 5'-terminal in two types of the primer to be used, cDNA strand in the side of 5'-terminal phosphorylated primer can be deleted by treating the amplified double-stranded polynucleotide with lambda exonuclease, etc., which can remove 5'-terminal phosphorylated DNA strand in the double-stranded DNA, to easily obtain the single-stranded tester polynucleotide bound (added) with the adapter.

In the present invention, among the methods for binding (adding) adaptor to the single-stranded tester polynucleotide, the method for amplifying complementary and/or homologous polynucleotide to the polynucleotide, to which the adapter (primer) is bound (added), by known amplification method such as PCR method, LAMP method, ICAN method, etc. using the primer designed based on the adaptor sequence as a template using polynucleotide existing in the tester, is preferable.

Consequently, in the present invention, a method for obtaining adaptor bound (added) single-stranded tester nucleotide is preferably the method comprising such step that (1''') after amplifying the tester derived double-stranded polynucleotide by using the primer designed based on the adaptor sequence, the double-stranded polynucleotide is converted to the single-stranded polynucleotide by enzymatic treatment.

The single-stranded tester polynucleotide bound (added) with the adapter can be obtained, for example, by the following method.

(1) Using cDNA library prepared by mRNA extracted from the tester by known methods (a method of Gubler et al. (Gulber, U. and Hoffman, B. J. (1983) Gene. 25, 263-269)) as a template or commercially available cDNA library, two types of primer such as a 5'-terminal phosphorylated primer and non-phosphorylated primer, designed by the known sequence derived from the vector in both ends of cDNA insertion fragment inserted into the vector are prepared, and the double-stranded cDNA derived from the tester gene is amplified by using the two primers with the cDNA, which is inserted into the vector, as a template by means of PCR method, LAMP method or ICAN method. Subsequently, the amplified double-stranded cDNA added with the primer (adaptor) is treated with the enzyme, which removes 5'-terminal phosphorylated DNA strand of the double-stranded DNA such as lambda exonuclease, etc. to remove cDNA strand in the 5'-terminal phosphorylated primer side to obtain the adaptor bounded (added) single-stranded tester cDNA (Higuchi R G, Ochman H. Nucleic Acid Research. 1989 Jul. 25; 17(14):5865, etc.).

(2) Two types of primers, which are the 5'-terminal phosphorylated primer and non-phosphorylated primer and are designed by the known sequence (adaptor), are prepared. Using the primers, cDNA added with adaptor sequences at 5'-terminal and 3'-terminal is prepared according to the oligo capping method. Subsequently, the primer is prepared by 5'-terminal and 3'-terminal adaptor sequences, and the double-stranded cDNA is amplified by means of PCR method, LAMP method, ICAN method, etc., then the amplified adaptor added double-stranded cDNA is treated by, for example, enzyme, which removes 5'-terminal phosphorylated DNA strand of the double-stranded DNA, such as lambda exonuclease, to remove cDNA strand of the 5'-terminal phosphorylated primer side to obtain adaptor bound (added) single-stranded tester cDNA (Higuchi R G, Ochman H. Nucleic Acid Research. 1989 Jul. 25; 17(14):5865, etc.).

(3) An objective polynucleotide is inserted into a suitable plasmid, and the polynucleotide fragment containing the objective inserted polynucleotide is cut out so that the one side of the polynucleotide fragment is prepared as 5'-protruding terminal (e.g. EcoR I, etc.) and the other side is prepared as 3'-terminal recessive end (e.g. Pst I, etc.) by utilizing multicloning side of the plasmid, thereafter the polynucleotide fragment is digested by the enzyme having 3'→5' exonuclease activity, which recognizes 5'-protruding terminal such as exonuclease III to obtain the single-stranded cDNA (Guo L H, Wu R. Methods in Enzymology. 1983; 100:60-96, etc.).

In this connection, among the above methods, methods (1) and (2) are preferable.

The thus obtained single-stranded tester polynucleotide is preferably purified by known purification method such as extraction with phenol/chloroform mixture, phenol/chloroform/isoamyl alcohol mixture, and/or chloroform/isoamyl alcohol mixture; alcohol precipitation; purification by using column; filtration by using filter; and the like.

(2) Polynucleotide Derived from Driver

A polynucleotide derived from driver of the present invention (hereinafter, designated as driver polynucleotide) can be any of a single-stranded polynucleotide or a double-stranded polynucleotide, and the double-stranded polynucleotide is preferable.

When the driver polynucleotide is a single-strand, quite naturally, the single-stranded driver polynucleotide is able to be the complementary strand with the single-stranded tester polynucleotide. Namely, when the tester polynucleotide is a sense strand, the driver polynucleotide is an antisense strand, when the tester polynucleotide is an antisense strand, the driver polynucleotide is a sense strand.

Further, the driver polynucleotide can be any of DNA and RNA, and is preferably DNA. Among them, genomic DNA and cDNA derived from mRNA existing in the driver (that is to say, cDNA synthesized by using mRNA extracted from the driver as a template) are preferable, and cDNA is particularly preferable.

The driver polynucleotide of the present invention can be obtained, as described hereinabove, by known methods used in this field such as a method for preparing double-stranded polynucleotide used for preparing the tester polynucleotide, a method for preparing single-stranded polynucleotide, and the like, and by using commercially available kits.

Among them, a method for amplifying polynucleotide complementary and/or homologous to the polynucleotide existing in the driver by known amplification method such as PCR method, LAMP method, ICAN method, etc. with the polynucleotide existing in the driver as the template is preferable.

Further, to the driver polynucleotide used in the present invention, an adaptor having known sequence may be bound (added) at the 5'-terminal and/or 3'-terminal, as in the single-stranded tester polynucleotide, and in that case, at least the adaptor is different from the known sequence, to which the primer for PCR performed in the step (3) hereinbelow is bound, in the single-stranded tester polynucleotide. In other words, the adaptor consisting of known sequence, to which the primer for PCR performed in the step (3) hereinbelow is not bound, may be bound (added) with the driver polynucleotide, however it is preferable that the driver polynucleotide does not contain the known sequence containing the adaptor bound (added) to the single-stranded tester nucleotide, or does not contain a part of sequence of the adaptor consisting of base number, which can function as a primer by itself, (namely, does not bound (added) with adaptor). Further, binding the non-complementary adaptor to the both terminal is preferable.

The driver polynucleotide can be obtained, for example, by the following methods.

(1) Using cDNA library prepared by mRNA extracted from the driver by known methods (a method of Gubler et al. (Gulber, U. and Hoffman, B. J. (1983) Gene. 25, 263-269)) as a template or commercially available cDNA library, two types of primer designed by known sequence derived from the vector in both ends of cDNA insertion fragment inserted into the vector are prepared, and the double-stranded cDNA derived from the driver gene is amplified by using the two primers with the cDNA, which is inserted into the vector, as a template by PCR method, LAMP method or ICAN method to obtain the adaptor bounded (added) double-stranded driver cDNA.

(2) From both terminals of the insertion fragment cDNA to the amplified primer (adaptor) in the adaptor bounded (added) double-stranded cDNA amplified by the above (1), is cleaved by appropriate restriction enzyme utilizing the restriction site in the multicloning site of both sides of the insertion fragment to obtain double-stranded diver cDNA constituted with the insertion fragment alone (the double-stranded driver cDNA without binding (adding) adaptor). In this connection, this method is useful when same primer is used in the tester polynucleotide and the driver polynucleotide (in case of binding the same adaptor), for example, vectors constructing cDNA library in the tester-derived cDNA library and in the driver-derived cDNA library are of the same series (for example, both vectors are pUC plasmid).

In addition, when the above method is used, attention should be paid in the following points.

Namely, when same primer is used in the tester polynucleotide and the driver polynucleotide (in case of binding the same adaptor), for example, when vectors constructing cDNA library in the tester-derived cDNA library and in the driver-derived cDNA library are of the same series (for example, both vectors are pUC plasmid), if a length from the terminal of the inserted cDNA fragment to the primer, in other words, if a chain length from the terminal of the primer to the primer binding with the insertion fragment is 100 bp or more, it becomes difficult to remove the fragment from the both terminals of the cleaved insertion fragment cDNA to the amplified primer (adaptor) by the purification method described hereinbelow. In that case, the cleaved fragment is hybridized with the complementary region existing in the tester to form a double-stranded hybrid, resulting that the adaptor region of the tester (region for annealing the primer for PCR) is removed in the step (2) described hereinbelow of the present invention, thereby amplification of the objective single-stranded tester specific polynucleotide in the step (3) is disturbed. Consequently, in such case, it is preferable that the cleavage from the both terminals of the insertion fragment cDNA to the amplified primer (adaptor) is performed by using a plurality types of restriction enzyme, or the fragment from the cleaved both terminals of the insertion fragment cDNA to the amplified primer (adaptor) is cleaved by using other restriction enzyme, so that the chain length from the cleaved both terminals of the insertion fragment cDNA to the amplified primer (adaptor) becomes 100 bp or less.

(3) Two types of primers, which are the primer of the complementary strand with the 5'-terminal phosphorylated single-stranded tester cDNA and the primer of the homologous strand with the non-phosphorylated single-stranded tester cDNA, designed according to the known sequence (adaptor) are prepared (i.e. the phosphorylated primer and the non-phosphorylated primer are so designed as to become the complementary strand with the single-stranded tester cDNA to be prepared. In other words, two primers (i.e. the phosphorylated primer and the non-phosphorylated primer) are so designed as to generate the 5'-terminal phosphorylated single-stranded tester cDNA and the complementary 5'-terminal non-phosphorylated single-stranded cDNA), and using these primers, cDNA added with the specific primer (adaptor sequence) to the 5'-terminal and 3'-terminal is prepared according to oligo capping method (Maruyama, K. and Sugano, S. (1994) Gene. 138, 171-174). Subsequently, the primer is prepared with 5'-terminal and 3'-terminal adaptor sequences, and the double-stranded cDNA is amplified by means of PCR method, LAMP method, ICAN method, etc., then the amplified adaptor added double-stranded cDNA is treated with the enzyme, which removes 5'-terminal phosphorylated DNA strand of the double-stranded DNA, such as lambda exonuclease, and the cDNA strand in the side of the 5'-terminal phosphorylated primer is removed to obtain the cDNA complementary to the single-stranded tester cDNA (i.e. the adaptor bound (added) single-stranded driver cDNA).

(4) An objective polynucleotide is inserted into a suitable plasmid, and the polynucleotide fragment containing the objective inserted polynucleotide is cut out so that the one side of the polynucleotide fragment is prepared as 5'-protruding terminal (e.g. EcoR I, etc.) and the other side is prepared as 3'-terminal recessive end (e.g. Pst I, etc.) by utilizing multicloning side of the plasmid, thereafter the polynucleotide fragment is digested by the enzyme having 3'→5' exonuclease activity, which recognizes 5'-protruding terminal such as exonuclease III to obtain the single-stranded cDNA (Guo L H, Wu R. Methods in Enzymology. 1983; 100:60-96, etc.).

Among the above methods, method (2) is preferable.

In this connection, the thus obtained single-stranded or double-stranded driver polynucleotide is preferably purified by known purification method such as extraction with phenol/chloroform mixture, phenol/chloroform/isoamyl alcohol mixture, and/or chloroform/isoamyl alcohol mixture; alcohol precipitation; purification by using column; filtration by using filter; and the like.

(3) Hybridization with Polynucleotide Derived from Tester and Polynucleotide Derived from Driver (Step (1))

Using the polynucleotide prepared by the above step, a hybridization (so called subtractive hybridization) is performed (i) between the single-stranded tester polynucleotide and the single-stranded driver polynucleotide to be the complementary strand with the single-stranded tester polynucleotide, or (ii) between the single-stranded tester polynucleotide and the double-stranded driver polynucleotide.

As a result of the hybridization hereinabove, the single-stranded tester polynucleotide having a complementary sequence in the driver polynucleotide [i.e. the tester polynucleotide existing in both of the tester and the driver (tester-nonspecific polynucleotide)] forms double-stranded polynucleotide (hybrid) with the tester polynucleotide and the complementary driver polynucleotide. On the other hand, the single-stranded tester polynucleotide having no complementary sequence in the driver polynucleotide (or existence amount is too small), (i.e. the tester-specific polynucleotide) does not form a hybrid to exist as the single-strand.

The hybridization can be performed by the method known in this field or by using commercially available kit.

For example, the single-stranded tester polynucleotide prepared as in the above is hybridized with an excess amount of the single-stranded or double-stranded driver polynucleotide to the tester polynucleotide in buffer containing proper amount of sodium salt, and if necessary, after thermal denaturation, at a proper temperature for proper time to form double-stranded polynucleotide (hybrid) of the tester polynucleotide and the complementary driver polynucleotide.

In the above, amount of the driver polynucleotide to be used is preferably larger than an amount of the tester polynucleotide, and amount of polynucleotide (amount of nucleic acid) in the case when the driver nucleotide to be used is a single-stranded is, although it cannot be the categorically because it varies depending on the target polynucleotide (gene) or intended use, generally 10 to 5,000 times, preferably 50 to 1,000 times, and more preferably 100 to 500 times of the amount of tester polynucleotide (amount of nucleic acid). Further, amount of polynucleotide (amount of nucleic acid) in the case when the driver nucleotide to be used is a double-stranded is generally 20 to 10,000 times, preferably 100 to 2,000 times, and more preferably 200 to 1000 times of the amount of tester polynucleotide (amount of nucleic acid).

The sodium salt to be used is that conventionally used in this field such as sodium chloride, sodium citrate, etc., and concentration to be used is also that conventionally used in this field, for example, selected as appropriate from a range of generally 20 mM to 2 M, preferably 50 mM to 1.5 M, and more preferably 100 mM to 1 M.

Further, the buffer to be used includes all buffers generally used in this field, for example, buffers having buffering action within a range of generally pH 5 to 9, preferably pH 6 to 8, and more preferably pH 6.5 to 7.5, such as Tris-HCl buffer, glycine buffer, Good's buffer (e.g. HEPES, PIPES, etc.). Concentration to be used is a concentration range generally used in this field, and selected as appropriate, for example, from a range generally 1 mM to 1 M, preferably 5 mM to 500 mM, and more preferably 10 mM to 100 mM.

In the above, thermal denaturation is performed generally at 90° C. to 105° C., preferably 93° C. to 103° C., and more preferably 95° C. to 100° C., and generally for 0.1 min. to 15 min., preferably for 0.5 min. to 10 min., and more preferably for 1 min. to 5 min. In this connection, in the above method, thermal denaturation is performed under the coexistence of the tester polynucleotide and the driver polynucleotide, but these may be performed individually. In this case, the sodium salt is not necessarily required. Further, in this case, it is preferable to perform hybridization by contacting the tester polynucleotide with the driver polynucleotide, after performing thermal denaturation and cooling with ice.

Conditions of the hybridization are not particularly limited but may be those according to the method conventionally used in this field. For example, the hybridization is performed under the presence of the sodium salt as described above, at a temperature within the lower limit of generally 30° C. or more, preferably 37° C. or more, more preferably 50° C. or more, further preferably 55° C. or more, particularly preferably 60° C. or more, and most preferably 65° C. or more, and the upper limit of generally 80° C. or less, preferably 75° C. or less, more preferably 70° C. or less, and generally for 1 min. to 30 hours, preferably 30 min. to 20 hours, and more preferably 1 hour to 16 hours.

In addition, in the above method, after performing hybridization, preferably the hybridization may be performed repeatedly by adding the driver polynucleotide in a concentration selected from the above-described concentration range, and by this method, hybridization can be performed under more stringent conditions.

In addition, in the above-described method, the reagents generally used in this field, for example, reagents such as organic solvents and the like, can be used.

(4) Removal of Hybridized Double-Stranded Polynucleotide (Step (2))

The hybridized double-stranded polynucleotide (i.e. double-stranded polynucleotide with the tester non-specific polynucleotide and the complementary driver polynucleotide) by the above-described step (1) of the present invention is removed by enzymatic treatment.

By this treatment, among the tester polynucleotides, a tester-non-specific polynucleotide, which is not specific to the tester but exists also in the driver, can be removed. Further, when the double-stranded driver polynucleotide is used, the annealed double-stranded polynucleotide (hybrid) with the driver polynucleotide and the driver polynucleotide is also removed simultaneously.

Enzyme to be used in the enzymatic treatment of the above step (2) of the present invention is an enzyme, which has a property not to decompose a single-stranded polynucleotide but dominantly decomposes a hybridized double-stranded polynucleotide, and is different depending on types of tester polynucleotide and driver polynucleotide used. For example, when the tester polynucleotide and the driver polynucleotide are both DNA (cDNA), deoxyribonuclease having a property of dominantly decomposing double-stranded DNA is used, and when one of the tester polynucleotide and the driver polynucleotide is DNA (cDNA) and the other is RNA, nuclease having a property of dominantly decomposing DNA-RNA hybrid is used. Further, when the tester polynucleotide and the driver polynucleotide is both RNA, ribonuclease having a property of dominantly decomposing double-stranded RNA is used. Enzymatic treatment using such nuclease leads to decomposition of the hybridized double-stranded polynucleotide (and the annealed double-stranded polynucleotide of the driver polynucleotide and the driver polynucleotide) generated by the above-described step (1) of the present invention, and as a result, the hybridized double-stranded polynucleotide (i.e. the tester-non-specific polynucleotide, which is not specific to the tester but exists in the driver) can be removed.

Further, when the tester polynucleotide is DNA (cDNA) and the driver polynucleotide is RNA, deoxyribonuclease having a property of dominantly decomposing DNA in the DNA-RNA hybrid can also be used, and when the tester polynucleotide is RNA and the driver polynucleotide is DNA (cDNA), ribonuclease (e.g. RNase H, etc.) having a property of dominantly decomposing RNA in the DNA-RNA hybrid can also be used. When these nucleases are used to perform enzymatic treatment, the hybridized double-stranded polynucleotide (and the annealed double-stranded polynucleotide of the driver polynucleotide and the driver polynucleotide) itself generated by the above described step (1) of the present invention cannot be decomposed, however, since the tester polynucleotide in the hybridized double-stranded polynucleotide can be decomposed, and as a result, the tester-non-specific polynucleotide, which is not specific to the tester but exists in the driver, can be removed.

Among the above-described nucleases, deoxyribonuclease having a property of decomposing dominantly the double-stranded DNA is preferable. Such nuclease includes, for example, double-strand specific DNA nuclease (Duplex-specific nuclease: DSN), etc. Origin of such enzyme is not particularly limited, but is, for example, marine invertebrate such as marine Crustacea (shrimp, crab, etc.) and sea urchin. Among them, double-strand specific DNA nuclease derived from marine Crustacea is preferable, in particular, double-strand specific DNA nuclease derived from Kamchatka crab (Paralithodes camtschaticus) is more preferable.

In this connection, the double-strand specific DNA nuclease can be produced according to the known method (e.g. Shagin D A, Rebrikov D V, Kozhemyako V B, Altshuler I M, Shcheglov A S, Zhulidov P A, Bogdanova E A, Staroverov D B, Rasskazov V A, Lukyanov S.: Genome Research. 2002 December; 12(12):1935-42), and commercially available product (e.g. Evrogen Inc.) can also be used.

Amount of nuclease to be used is not particularly limited so long as the amount can sufficiently decompose hybridized double-stranded polynucleotide. Specifically, although the amount cannot be categorically the because it varies depending on the type of nuclease used, for example, when double-strand specific DNA nuclease is used as nuclease, generally it is 0.01 u/µl to 10 u/µl, preferably 0.1 u/µl to 5 u/µl, and more preferably 0.5 u/µl to 1 u/µl for total polynucleotide 1 µg.

As for conditions for the enzymatic treatment (temperature, time, pH, etc.), namely, as for conditions for contacting the hybridized double-stranded polynucleotide with nuclease, although they cannot categorically be the because they vary depending on types of nuclease used, but the polynucleotide and the nuclease may be treated within a time sufficiently decomposing the generated hybrid (or tester polynucleotide in the hybrid) at around the optimum temperature and the optimum pH of the nuclease generally used.

More specifically, for example, when double-strand-specific DNA nuclease is used as a nuclease, the treatment is performed under such conditions as at a temperature within the lower limit of generally 20° C. or more, preferably 30° C. or more, more preferably 50° C. or more, further preferably 55° C. or more, particularly preferably 60° C. or more, and most preferably 65° C. or more, and the upper limit of generally 80° C. or less, preferably 75° C. or less, and more preferably 70° C. or less, and generally at pH 6 to 9, preferably pH 6.5 to 8.5, more preferably pH 7 to 8, generally for 0.5 min. to 60 min., preferably 1 min. to 45 min., and more preferably 5 min. to 30 min.

Further, in order to maintain the above pH range, a buffer generally used in this field can be used. Such buffer is not particularly limited so long as it has a buffer action in the pH range as described in the above, and includes, for example, Tris-HCl buffer, glycine buffer and Good's buffer (e.g. HEPES, PIPES, etc.). Concentration to be used is within a range of concentration generally used in this field. For example, the concentration is selected as appropriate, from a ranges of 1 mM to 500 mM, preferably 5 mM to 100 mM, and more preferably 10 mM to 50 mM.

In this connection, after performing enzyme treatment as described above, termination of the enzyme reaction may be performed by the presence of a reaction terminator, for example, a chelating agent such as EDTA, etc. in the reaction mixture obtained by performing enzymatic treatment.

Presence of such reaction terminator in the reaction mixture may be realized, for example, by containing the reaction terminator in water or in the buffer as described hereinabove, and admixing the solution containing the reaction terminator and the reaction solution obtained by performing enzyme treatment.

Time for terminating the reaction is generally 0.1 min. to 30 min., preferably 0.5 min. to 20 min., and more preferably 1 min. to 10 min.

Further, temperature for terminating the reaction is not particularly limited, but preferably 50° C. to 90° C., preferably 60° C. to 80° C., and more preferably 65° C. to 75° C.

The enzymatic treatment is performed by contacting the hybridized double-stranded polynucleotide prepared by the step (1) of the present invention as described hereinabove with the above-described nuclease.

Such method is not particularly limited so long as the hybridized double-stranded polynucleotide can be finally in contact with the nuclease, but the treatment is generally performed by adding and admixing a solution containing the nuclease to the hybridization solution obtained by performing the above-described step (1) of the present invention.

In the above description, the solution in which the nuclease is contained is not particularly limited so long as the solution does not inhibit decomposing action of the nuclease, and includes a solution conventionally used in this field such as water and the above-described buffer, and concentration thereof in use and the like may be selected, as appropriate, from the above-described concentration range.

Here, besides the nuclease, a sodium salt, an activator conventionally used in this field (metal ion such as magnesium ion, etc.), a stabilizer (glycerol, thiol compound such as dithiothreitol, mercaptoethanol, etc.), an antiseptic, etc. may be contained in the solution. In this connection, these sodium salt, activator, stabilizer, antiseptic, etc. may be contained in a solution as described above separately from the solution containing the nuclease. In this case, the solution containing the nuclease and one or more kinds of solutions containing sodium salt, activator, stabilizer or antiseptic are separately added to the hybridization solution. Among them, a sodium salt is preferably contained.

The sodium salt to be used is a salt conventionally used in this field, for example, sodium chloride, sodium citrate, etc., and concentration to be used is selected, as appropriate, from a concentration range used conventionally in this field, for example, generally 20 mM to 2 M, preferably 50 mM to 1.5 M, and more preferably 100 mM to 1 M.

For example, when double-strand-specific DNA nuclease is used as the nuclease, the enzymatic treatment (step (2) of the present invention) is performed as follows.

A solution containing double-strand-specific DNA nuclease and a solution containing activator and stabilizer are admixed to the hybridization solution obtained by performing the step (1) of the present invention, and treated (reacted) under the conditions described hereinabove to remove the hybridized double-stranded polynucleotide (the double-stranded polynucleotide of the tester polynucleotide and the complementary driver polynucleotide, or the annealed double-stranded polynucleotide of the driver polynucleotide and the driver polynucleotide) existing in the hybridization solution by decomposition.

Further, in the above, preferable activator is magnesium ion. Origin thereof is for example magnesium salt such as magnesium chloride, magnesium sulfate, etc., and among them, magnesium chloride is preferable. Further, amount of magnesium salt may be an amount which can sufficiently activate the double-strand-specific DNA nuclease, and generally 0.1 mM to 100 mM, preferably 0.5 mM to 50 mM, and more preferably 1 mM to 10 mm.

Further, with regard to the stabilizer, for example, a thiol compound such as dithiothreitol, mercaptoethanol, etc. is preferable, and among them, dithiothreitol is preferable. Further, amount thereof in use may be the amount which can stabilize the double-strand specific DNA nuclease, and generally 0.01 mM to 10 mM, preferably 0.1 mM to 5 mM, and more preferably 0.5 mM to 1 mM.

In this connection, the step (1) and the step (2) are preferably performed at as high temperature as possible. For example, the step (1) and the step (2) of the present invention are performed respectively at a temperature within the lower limit of preferably 50° C. or more, more preferably 55° C. or more, particularly preferably 60° C. or more, and most preferably 65° C. or more, and the upper limit of generally 80° C. or less, preferably 75° C. or less, and more preferably 70° C. or less. When the step (2) is performed following the step (1), the step is performed without decreasing temperature once from the above-described temperature range, while the temperature is maintained in the above-described temperature range without decreasing temperature once from the above-described temperature range.

According to the above-described method of the present invention [the step (1) and the step (2) of the present invention], the tester-specific polynucleotide can be obtained by decomposing and removing the tester-non-specific polynucleotide among polynucleotides existing in the tester.

In this connection, in the reaction mixture obtained by performing the step (2) of the present invention, besides the non-hybridized single-stranded tester specific polynucleotide, the non-hybridized single-stranded driver polynucleotide coexists. The coexisting non-hybridized single-stranded driver polynucleotide can be removed by known isolation (separation) treatment or purification treatment, and only the single-stranded tester specific polynucleotide can be isolated.

Such method includes, for example, a method in which the single-stranded tester-specific polynucleotide is converted to the double strand with Klenow fragment by using the primer, which is designed based on the adaptor sequence existing only in the tester-specific polynucleotide such as the primer for amplifying the tester cDNA, and the double strand is cleaved by restriction enzyme within the adaptor sequence of both ends, then is inserted into the suitable vector, thereby transforming only the tester-specific polynucleotide (cDNA); and a method in which the primer, which is designed based on the adaptor sequence existing only the tester-specific polynucleotide such as the primer for by amplifying the tester cDNA, is labeled with biotin, and after annealing with the tester-specific polynucleotide (cDNA), binding with the solid phase such as streptavidin beads, etc. to isolate tester-specific polynucleotide, and the like.

In addition, the non-hybridized single-stranded driver polynucleotide is, in the case when the single-stranded driver polynucleotide complementary to the tester polynucleotide is used, the single-stranded polynucleotide specific to the driver and the single-stranded driver polynucleotide existing in both of the tester and the driver, which is not hybridized with the tester non-specific polynucleotide, and in the case when the double-stranded driver polynucleotide is used, the single-stranded polynucleotide specific to the driver, which is existed as the single strand without annealing (two types of complementary strand and homologous strand to the tester polynucleotide) and the single-stranded driver polynucleotide existing in both of the tester and the driver existing as the single strand without annealing (two types of complementary strand and homologous strand to the tester polynucleotide).

2-2. Method for Amplifying Tester-Specific Polynucleotide of the Present Invention The tester-specific polynucleotide can be concentrated by amplifying the thus obtained tester-specific polynucleotide.

(1) Amplification of Non-Hybridized Single-Stranded Tester Specific Polynucleotide [Step (3)]

The single-stranded tester-specific polynucleotide obtained by the method for obtaining of the present invention can be obtained in large amount.

Namely, only the single-stranded tester-specific polynucleotide remaining after performing the step (2) of the present invention is substantially amplified.

According to this method, even in the case when the single-strand tester specific polynucleotide is not subjected to isolation (separation) treatment or purification treatment after performing the step (2) of the present invention, only the single-stranded tester-specific polynucleotide can be concentrated because the non-hybridized single-stranded driver polynucleotide coexisting with the single-stranded tester-specific polynucleotide is substantially not amplified.

In the present invention, amplifying the single-stranded tester-specific polynucleotide means (1) a case when only the complementary strand to the single-stranded tester-specific polynucleotide is amplified, or (2) a case when the double-strand of the single-stranded tester-specific polynucleotide and the complementary strand thereof are amplified.

Method of such amplification is not particularly limited so long as the single-stranded tester-specific polynucleotide obtained by the method of the present invention [(1) the complementary strand to the single-stranded tester-specific polynucleotide alone, or (2) the double-strand of the single-stranded tester-specific polynucleotide and the complementary strand thereof] can be amplified, and the amplification can be performed according to the known amplification method of polynucleotide conventionally used in this field. Such known amplification method of polynucleotide includes, for example, PCR method [oligo-capping method: a simple method to replace the cap structure of eukaryotic mRNAs with oligoribonucleotides, Kazuo Maruyama and Sumio Sugano, Gene, 138 (1994) 171-174; SMART method: Diatchenko, L., et al. Proc. Natl. Acad. Sci. USA 91:6025-6030 (1996); Gene trapper method: High-efficiency full-length cDNA cloning by biotinylated CAP trapper, Carninci P, Kvam C, Kitamura A, Ohsumi T, Okazaki Y, Itoh M, Kamiya M, Shibata K, Sasaki N, Izawa M, Muramatsu M, Hayashizaki Y, Schneider C., Genomics. 1996 Nov. 1; 37 (3): 327-36; RACE method: Determination of 5' ends of specific mRNAs by DNA ligase-dependent amplification, Bertling W M, Beier F, Reichenberger E., PCR Methods Appl. 1993 October; 3(2): 95-9], LAMP method (Loop-mediated isothermal amplification of DNA, Notomi T, Okayama H, Masubuchi H, Yonekawa T, Watanabe K, Amino N, Hase T. Nucleic Acids Res. 2000 Jun. 15; 28(12):E63), and ICAN method [Development of the detection system for *Mycobacterium tuberculosis* DNA by using the isothermal DNA amplification method ICAN, Shimada M, Hino F, Sagawa H, Mukai H, Asada K, Kato I. Rinsho Byori. 2002 May; 50(5): 528-32], and the like. Among them, PCR is preferable.

In this connection, various amplification conditions (temperature, time, pH, number of cycles, etc.) may be performed according to the above-described known method. Further, enzymes and reagents to be used may be those used in the known methods.

Further, the amplification can also be performed by using commercially available kit.

The primer to be used in the amplification is not particularly limited so long as the primer can amplify the single-stranded tester-specific polynucleotide obtained by the method of the present invention ((1) the complementary strand to the single-stranded tester-specific polynucleotide alone, or (2) the double-strand of the single-stranded tester-specific polynucleotide and the complementary strand thereof).

Namely, the primer may be designed and prepared, for example, depending upon the objective amplification method and conditions thereof, or considering the melting temperature (Tm value), etc. The primer is preferably those having a length of 15 bases to 60 bases, preferably 20 bases to 35 bases, more preferably 25 bases to 30 bases, which is thought to be a necessary base number for maintaining specificity of the primer sequence.

For example, when the single-stranded tester-specific polynucleotide is isolated by the isolation (separation) treatment or the purification treatment as described above after performing the step (2) of the present invention, since the tester-non-specific polynucleotide or the non-hybridized driver polynucleotide other than the single-stranded tester-specific polynucleotide does not coexist, any type of primer can be used.

Such the primer includes, for example, when the tester polynucleotide bound (added) with adapter as described above is used, the primer designed and prepared based on the adaptor sequence, and for example, when the tester cDNA is prepared from the cDNA library, one type or two or more types of primers designed and prepared based on the sequence derived from the vectors in both terminal of cDNA insertion fragment (i.e. oligonucleotide containing the adaptor sequence consisting of the sequence, which is not existing in the polynucleotide derived from the driver as described hereinbefore or oligonucleotide containing a part of the complementary sequence or the entirety thereof).

Further, for example, when the single-stranded tester-specific polynucleotide is not isolated without performing the isolation (separation) treatment or the purification treatment, after performing the step (2) of the present invention, the tester-non-specific polynucleotide is not coexisting but the non-hybridized single-stranded tester polynucleotide is coexisting therewith. However, in such case, only the single-stranded tester-specific polynucleotide can be amplified by using the primer designed and prepared based on the sequence which is existing in only the single-stranded tester-specific polynucleotide and not existing in the polynucleotide derived from the driver.

Such primer includes, for example, one type or two or more types of primers designed and prepared based on the adaptor consisting of the sequence, which does not exist in the polynucleotide derived from the driver as described hereinbefore (i.e. oligonucleotide containing the adaptor sequence consisting of the sequence, which is not existing in the polynucleotide derived from the driver as described hereinbefore or oligonucleotide containing a part of the complementary sequence or the entirety thereof), and the like.

Further, as examples of two or more types of primers for using in PCR, oligonucleotides containing a part or entirety of the non-complementary adaptor sequence, or oligonucleotides containing a part or entirety of the complementary sequence thereof, namely two or more types of primers different from each other, are preferable.

The primer may be labeled with labeling substance. As the labeling substance used for labeling the primer with the labeling substance, any known labeling substance such as radioisotope ($^{32}P$, $^{33}P$, $^{35}S$, etc.), enzyme (alkaline phosphatase, horseradish peroxidase, etc.), fluorescent substance (cyanine-based dyes such as Cy3, Cy5 (Amersham Bioscience Inc.), fluorescein, etc.), luminescent substance (chemiluminescent reagent containing acridinium ester, etc.) and biotin can be used. Further, labeling of the primer with the labeling substance can be performed by the labeling methods conventionally known in this field, including, for example, a method for labeling the primer by incorporating nucleotide labeled with radioisotope or fluorescent substance in the synthesis of the primer; a method for labeling the primer with radioisotope after synthesis of the primer (a random primer method, a nick-translation method, a method of 5'-terminal labeling using T4-polynucleotide, a method of 3'-terminal labeling using terminal deoxynucleotide transferase, and RNA labeling method); a direct labeling method wherein the enzyme is directly bonded by a covalent bond to the primer to be labeled; a method for labeling the nucleotide with fluorescent substance, wherein a nucleotide having a linker arm is substituted as a member of oligonucleotide in the sequence; a method for labeling nucleotide with luminescent label or biotin label, and the like.

Although the single-stranded tester-specific polynucleotide can be amplified by the step (3) of the present specification, when the single-stranded tester-specific polynucleotide is not subjected to isolation (separation) treatment or purification treatment after performing the step (2) of the present invention, namely, when the non-hybridized single-stranded tester-specific polynucleotide is amplified in the reaction mixture coexisting with the non-hybridized single-stranded tester-specific polynucleotide and the non-hybridized single-stranded driver polynucleotide obtained by performing the step (2) of the present invention, the non-hybridized single-stranded driver polynucleotide is coexisting besides the non-hybridized single-stranded tester-specific polynucleotide amplified in the reaction mixture obtained by performing the step (3) of the present invention. However, in this case, the amplified single-stranded tester-specific polynucleotide can be isolated by the step of removing the single-stranded polynucleotide in the step (4) of the present invention described hereinafter.

In particular, in the case when the step of removing the single-stranded polynucleotide in the step (4) of the present invention described hereinafter is the step of removing the single-stranded polynucleotide by enzymatic treatment, the tester-specific polynucleotide amplified in the step (3) of the present invention is preferably the double-strand, since the amplified tester-specific polynucleotide can be easily isolated by enzymatic treatment to specifically decompose and remove the single-stranded polynucleotide.

Method for obtaining amplified double-stranded tester-specific polynucleotide includes, for example, among the known amplification methods described above, a method for amplifying the double-strand of the single-stranded tester-specific polynucleotide and the complementary strand thereof.

Further, among the known amplification methods described above, in the case when only the complementary strand to the single-stranded tester-specific polynucleotide is amplified, using the complementary strand to the amplified single-strand-specific polynucleotide, for example, the double-stranded tester-specific polynucleotide can be obtained by the following methods:

(a) a method comprising using the complementary strand to the amplified single-stranded tester-specific polynucleotide as a template, amplifying the complementary strand to the complementary strand to the amplified single-stranded tester-specific polynucleotide by performing RCR again using the complementary primer to the amplified single-stranded tester-specific polynucleotide, and obtaining the double-strand of the single-stranded tester-specific polynucleotide and the complementary strand thereof; and (b) a method comprising using the complementary strand to the amplified single-stranded tester-specific polynucleotide as a template, subjecting to the primer extension of the complementary strand to the complementary strand to the amplified single-stranded tester-specific polynucleotide by using the complementary primer to the amplified single-stranded tester-specific polynucleotide and polymerase such as Klenow fragment, and obtaining the double-strand of the single-stranded tester specific polynucleotide and the complementary strand thereof, and the like.

Among them, the method amplifying the double strand of the single-stranded tester-specific polynucleotide and the complementary strand thereof is preferable.

In this connection, in the above, no special treatment is required for forming the double-strand hybrid of the double-stranded tester-specific polynucleotide obtained, for example, a solution containing the obtained single-stranded tester specific polynucleotide and the complementary strand thereof is maintained generally at 30° C. to 80° C., preferably at 37° C. to 75° C., and more preferably at 50° C. to 70° C. to form a hybrid thereof.

As described hereinabove, in the present invention, amplifying the double strand of the single-stranded tester-specific polynucleotide and the complementary strand thereof is preferable.

Consequently, the amplification method of the tester-specific polynucleotide of the present invention is preferably the method comprising (3') the step for obtaining the double-stranded polynucleotide derived from the tester by amplifying the non-hybridized single-stranded polynucleotide derived from the tester and the complementary strand thereof.

For example, the non-hybridized single-stranded tester-specific polynucleotide can be amplified by the following method.

Namely, (a) to the reaction mixture obtained by performing the step (2) of the present invention, and if necessary, to the solution containing the single-strand tester-specific polynucleotide isolated by further isolation treatment or purification treatment, each different two types of primer and deoxyribonucleotide triphosphate (dATP, dCTP, dGTP and dTTP) as described hereinabove are suitably added, and the resultant solution is heated at suitable temperature for suitable time to denature by heat. (b) After heating, the solution is cooled to anneal the primer to the single-stranded tester-specific polynucleotide (or the single-stranded tester-specific polynucleotide and amplified complementary polynucleotide thereof). (c) Subsequently, the suitable polymerase is reacted at suitable temperature for suitable time to extend the primer, thereby the complementary strand to the single-stranded tester-specific polynucleotide (or the complementary strand to the single-stranded tester specific polynucleotide, and the complementary strand to the amplified polynucleotide complementary to the single-stranded tester specific polynucleotide) is synthesized (amplified). The non-hybridized single-stranded tester-specific polynucleotide and the complementary strand thereof are amplified by repeating the above step from (a) to (c) for suitable times (e.g. generally 5 times to 60 times, preferably 10 times to 50 times, and more preferably 15 times to 40 times).

In the above method, amount of reagents to be used, type and amount of polymerase, reaction conditions, etc. may be selected, as appropriate, according to the known methods as described above.

For example, thermal denaturation of the above step (a) is performed generally at 90° C. to 105° C., preferably at 93° C. to 103° C., and more preferably at 95° C. to 100° C., and generally for 0.01 min. to 10 min., preferably for 0.05 min. to 5 min., and more preferably for 0.1 min. to 2 min. Further, annealing in the step (b) is performed generally at 30° C. to 75° C., preferably at 40° C. to 72° C., and more preferably at 50° C. to 68° C., and generally for 0.01 min. to 10 min., preferably for 0.05 min. to 5 min., more preferably for 0.1 min. to 2 min. Polymerase to be used in the above step (c) is not particularly limited and the enzyme conventionally used in this field may be used, and includes, for example, DNA polymerase such as DNA polymerase I, Klenow fragment, T4 DNA polymerase, and the like; heat-stable enzyme such as Taq DNA polymerase, Tth DNA polymerase, Pfu DNA polymerase, and the like; reverse transcriptase, etc. Further, conditions (temperature, time, etc.) for performing polymerase reaction can not be categorically said because they are different depending on types, etc. of polymerase used, but in the case when the non-heat-stable enzyme such as DNA polymerase I is used, these are generally at 20° C. to 50° C., preferably at 25° C. to 45° C., and more preferably at 30° C. to 37° C., and generally for 1 min. to 24 hours, preferably for 5 min. to 12 hours, and more preferably for 30 min. to 4 hours. For example, in the case when the heat-stable enzyme such as Taq DNA polymerase is used, these are generally at 30° C. to 85° C., preferably at 40° C. to 80° C., and more preferably at 50° C. to 75° C., and generally for 0.01 min. to 20 min., preferably for 0.05 min. to 15 min., and more preferably for 0.1 min. to 10 min.

Further, in the above method, deoxyribonucleotide triphosphate, primer, reagents, polymerase, etc, may be added after each step of (a) to (c).

Among them, when heat-stable enzyme such as Taq DNA polymerase, Tth DNA polymerase, Pfu DNA polymerase, and the like, is used, it is not necessary to add further deoxyribonucleotide triphosphate, primer, reagents, polymerase, etc, after each step of (a) to (c), and all reagents and polymerase can be present from the initial stage. Consequently, the heat-stable enzyme is particularly preferable.

The thus obtained double-stranded tester-specific polynucleotide is preferably purified by the known purification methods such as extraction, for example, with phenol/chloroform mixture, phenol/chloroform/isoamyl alcohol mixture, and/or chloroform/isoamyl alcohol mixture; alcohol precipitation; purification by using column; filtration by using filter; and the like.

(2) Removal of Non-Hybridized Single-Stranded Driver Polynucleotide (Step (4))

As described above, in the case when the tester-specific polynucleotide (single-strand or double-strand) amplified (concentrated) by the step (3) of the present invention is coexisting with the single-stranded driver polynucleotide, namely, in the case when the single-stranded tester-specific polynucleotide is not subjected to isolation (separation) treatment or purification treatment after performing the step (2) of the present invention, the non-hybridized single-stranded driver polynucleotide exists besides the amplified tester-specific polynucleotide [the non-hybridized single-stranded tester-specific polynucleotide in the step (2)] in the reaction mixture obtained by performing the step (3) of the present invention. In such case, the amplified tester-specific polynucleotide (single-strand or double-strand) can be isolated by removing the single-stranded driver polynucleotide.

Method for removing the single-stranded driver polynucleotide includes the known isolation (separation) method or the purification method as described hereinbefore.

Further, in the case when the amplified tester-specific polynucleotide is the double-stranded polynucleotide, the double-stranded tester-specific polynucleotide may also be isolated by specifically decomposing and removing the single-stranded polynucleotide (the single-stranded driver polynucleotide) coexisting with the double-stranded tester-specific polynucleotide by enzymatic treatment using an enzyme having a property to decompose the single-stranded polynucleotide but not to decompose the double-stranded polynucleotide (Convenient single-step, one tube purification of PCR products for direct sequencing. E Werle, C Schneider, M Renner, M Veolker, and W Fiehn, Nucleic Acids Res. 1994 Oct. 11; 22(20): 4354-4355, etc.).

Among the above methods, the method of removing (decomposing) single-stranded polynucleotide by enzymatic treatment is preferable.

Consequently, method for removing the single-stranded driver polynucleotide in the present invention is preferably a method comprising (4') the step for removing the non-hybridized single-stranded polynucleotide derived from the driver by enzymatic treatment.

Enzymes to be used in the enzymatic treatment are those having a property not to decompose hybridized double-stranded polynucleotide but to decompose dominantly the single-stranded polynucleotide, and are different depending on types of tester polynucleotide and driver polynucleotide to be used.

For example, in the case when the tester polynucleotide and the driver polynucleotide are concurrently DNA (cDNA), for example, deoxyribonuclease having a property not to decompose the double-stranded DNA but to decompose dominantly the single-stranded DNA such as single-strand-specific DNA nuclease (exonuclease I, exonuclease IX, etc.) is used. In the case when the tester polynucleotide and the driver polynucleotide are concurrently RNA, for example, ribonuclease having a property not to decompose the double-stranded RNA but to decompose dominantly the single-stranded RNA such as single-strand-specific RNA endonuclease (ribonuclease) (RNase A, RNase IV, RNase T1, RNase T2, RNase II, RNase III and RNase I) is used.

By performing the enzymatic treatment using such nuclease, the single-stranded driver polynucleotide (single-stranded driver-specific polynucleotide and single-stranded driver non-specific polynucleotide) coexisting with the double-stranded polynucleotide (double-stranded tester-specific polynucleotide) obtained in the step (3) of the present invention as described above can be decomposed and the double-stranded polynucleotide (double-stranded tester-specific polynucleotide) can be isolated.

Among nucleases described hereinabove, deoxyribonuclease having a property not to decompose the double-stranded DNA but to decompose dominantly the single-stranded DNA is preferable, and exonuclease I is more preferable.

Origin of the nuclease described above is not particularly limited, and the enzymes conventionally used in this field can be used. In this connection, the nuclease can be produced according to the known methods [e.g. Lehman, I R., Nussbaum, A. L., J. Bio. Chem., 239, 2628-2636, 1964], and commercially available products (e.g. products of New England Biolabs Inc.) can also be used.

Amount of nucleases to be used is not particularly limited so long as the amount can sufficiently decompose the single-stranded polynucleotide. Specifically, although it cannot be categorically said because it varies depending on types of nuclease to be used, for example, when the single-strand specific DNA nuclease is used as the enzyme, it is generally 0.1 u/µl to 100 u/µl, preferably 0.5 u/µl to 50 u/µl, and more preferably 1 u/µl to 10 u/µl to the tester polynucleotide 1 µg.

Conditions of the enzyme treatment (temperature, time, pH, etc.), namely, conditions in the reaction (contact) with the single-stranded polynucleotide and nuclease are different depending on types of the nuclease to be used and cannot be categorically said, but the enzyme treatment may be performed by treating for enough time to decompose sufficiently the single-stranded polynucleotide around at optimum temperature and optimum pH of the nuclease generally used.

More specifically, when the single-strand specific DNA nuclease is used as the nuclease, treatment is performed generally at 20° C. to 60° C., preferably 25° C. to 50° C., and more preferably 30° C. to 40° C., generally at pH 7 to 11, preferably pH 8 to 10.5, and more preferably pH 9 to 10, and generally for 0.1 min. to 60 min., preferably 0.5 min. to 45 min., and more preferably 1 min. to 30 min.

Further, in order to maintain the above pH range, a buffer generally used in this field can be used. Such buffer is not particularly limited so long as the buffer has buffering action in the pH range as described above, and includes, for example, Tris-HCl buffer, glycine buffer and Good's buffer (e.g. HEPES, PIPES, etc.). Concentration in use is selected, as appropriate, from a range of concentration generally used in this field, for example, generally 1 mM to 500 mM, preferably 5 mM to 250 mM, and more preferably 10 mM to 100 mM.

In addition, after performing the enzyme treatment as described above, in order to terminate the enzyme reaction, for example, a method using a reaction terminator, for example, chelating agents such as EDTA and/or a method employing heating treatment is used.

The method using a reaction terminator is performed in such way that, for example, the reaction terminator is containing in water or in the buffer as described hereinabove, and the solution containing the reaction terminator and the reaction solution obtained by performing the enzyme treatment are admixed, thereby to make the reaction terminator exist in the reaction solution obtained by the enzyme treatment.

The method for terminating the reaction by heating may be performed by treating the reaction solution obtained by the enzyme treatment generally at 60° C. to 90° C., preferably 65° C. to 85° C., and more preferably 70° C. to 85° C.

Reaction time by using a reaction terminator and time for heat treatment are generally 1 min. to 60 min., preferably 5 min. to 30 min., and more preferably 10 min. to 20 min.

In the above reaction termination method, combination of the method using a reaction terminator and the method using heat treatment is preferable.

The enzymatic treatment is performed by contacting the tester-specific polynucleotide amplified (concentrated) by the step (3) of the present invention as described hereinabove and the coexisting single-stranded driver polynucleotide with the above-described nuclease.

Such method is not particularly limited so long as the method can finally contact the amplified (concentrated) tester-specific polynucleotide and the coexisting single-stranded driver polynucleotide with the nuclease, and the treatment is performed generally by such method that the solution containing the nuclease is admixed with the reaction mixture obtained by performing the above described step (3) of the present invention.

In the above, the solution in which the nuclease is contained may be those not to inhibit the decomposing action of the nuclease, and the solution includes those conventionally used in this field such as water and the above-described buffer, and concentration thereof in use may be selected, as appropriate, from the concentration range described above.

Here, besides the nuclease, an activator (metal ion such as magnesium ion, etc.), a stabilizer (thiol compound such as dithiothreitol, mercaptoethanol, etc.), an antiseptic, etc. conventionally used in this field may be added to the solution. In this connection, the activator, stabilizer, antiseptic, etc. may be contained in a solution as described above different from the solution containing the nuclease. In such case, the solution containing the nuclease and other one or more solutions containing activator, stabilizer or antiseptic are separately added to the reaction mixture.

For example, when single-strand specific DNA nuclease is used as the nuclease, the enzymatic treatment [step (4) of the present invention] is performed as follows.

A solution containing the single-strand specific DNA nuclease and the solution containing activator and stabilizer are admixed to the reaction mixture obtained by performing the step (4) of the present invention, and treated (reacted) under the conditions described hereinabove to decompose and remove the non-hybridized single-stranded driver polynucleotide (the single-stranded driver-specific polynucleotide and the single-stranded driver-non-specific polynucleotide) existing in the reaction mixture.

Further, in the above, preferable activator is magnesium ion. Origin thereof is, for example, magnesium salt such as magnesium chloride, magnesium sulfate, etc., and among them, magnesium chloride is preferable. Further, amount of magnesium salt to be used may be an amount, which can sufficiently activate the single-strand specific DNA nuclease, and is generally 0.1 mM to 100 mM, preferably 0.5 mM to 50 mM, and more preferably 1 mm to 10 mm.

With regard to the stabilizer, for example, thiol compound such as dithiothreitol, mercaptoethanol, etc. is preferable, and among them, dithiothreitol is preferable. Further, amount in use thereof may be an amount, which can stabilize the single-strand specific DNA nuclease, and is generally 0.01 mM to 100 mM, preferably 0.05 mM to 50 mM, and more preferably 0.1 mm to 10 mm.

As described hereinabove, the tester-specific polynucleotide amplified by the amplification method of the present invention (steps (1) to (3) of the present invention) can be easily isolated by the step (4) of the present invention.

Further, the step (4) of the present invention may be performed without performing the amplification of the step (3) by such method that after the single-stranded tester-specific polynucleotide obtained in the step (2) is converted to the double strand by a method comprising using the single-stranded tester-specific polynucleotide as a template, subjecting to the primer extension of the complementary strand to the single-stranded tester-specific polynucleotide by using the complementary primer to the single-stranded tester-specific polynucleotide and polymerase such as Klenow fragment, and obtaining the double strand of the single-stranded tester-specific polynucleotide and the complementary strand thereof. In this case, although the tester-specific polynucleotide can not be amplified (concentrated), the non-hybridized single-stranded driver polynucleotide coexisting with the single-stranded tester-specific polynucleotide obtained in the step (2) can be decomposed and removed, and only the single-stranded tester-specific polynucleotide can be isolated.

2-3. Specific Method of the Present Invention

An obtaining method or an amplifying method of the present invention can be performed according to the procedures of the chart illustrated in FIG. 1 by using the single-stranded tester polynucleotide and the single-stranded or double-stranded driver polynucleotide.

Namely, at first, the single-stranded tester polynucleotide, preferably the single-stranded tester polynucleotide added with adaptor is prepared from the intended sample, employing the known method, preferably the method of preparing the single-stranded polynucleotide by enzymatic treatment after preparing the double-stranded polynucleotide derived from the tester [the step (1') of the present invention], more preferably the method of preparing the single-stranded polynucleotide by enzymatic treatment of the double-stranded polynucleotide after amplifying the double-stranded polynucleotide derived from the tester [the step (1") of the present invention]. On the other hand, by applying the known method, the double-stranded driver polynucleotide or the single-stranded driver polynucleotide complementary to the single-stranded tester polynucleotide is prepared from another sample. Subsequently, for example, the obtaining method or the amplifying method of the present invention is performed by the following procedures.

(Procedure 1)

Hybridization is performed (i) between the single-stranded tester polynucleotide and the single-stranded driver polynucleotide to be the complementary strand to the single-stranded tester polynucleotide, or (ii) between the single-stranded tester polynucleotide and the double-stranded driver polynucleotide, and the double-stranded polynucleotide of the tester-non-specific polynucleotide and the driver polynucleotide complementary thereto (the driver-non-specific polynucleotide), or the hybrid and the annealed double-stranded polynucleotide of the driver polynucleotide and the driver polynucleotide is hybridized [step (1)]. Subsequently, the hybridized double-stranded polynucleotide is decomposed and removed by enzymatic treatment to remove the tester-non-specific polynucleotide or tester-non-specific polynucleotide and the annealed double-stranded driver polynucleotide [step (2)]. Further, if necessary, the coexisting non-hybridized single-stranded driver polynucleotide is removed by a known isolation (separation) method or a purification method [isolation step]. According to the above procedure, the single-stranded tester-specific polynucleotide can be obtained or isolated (obtaining method of the present invention 1).

(Procedure 2)

After performing the above step (1) and step (2), and if necessary, performing the isolation step, the obtained or isolated single-stranded tester-specific polynucleotide is amplified [step (3)]. According to this step, only the tester-specific polynucleotide is practically amplified and only the tester-specific polynucleotide can be obtained in large amounts (amplifying method of the present invention 1).

(Procedure 3)

After performing the above step (1) and step (2), the obtained single-stranded tester-specific polynucleotide is amplified [step (3)]. Subsequently, non-hybridized single-stranded driver polynucleotide coexisting with the amplified tester-specific polynucleotide is removed [step (4)]. According to this procedure, the amplified tester-specific polynucleotide can be isolated (amplifying method of the present invention 2).

(Procedure 4)

According to the procedure hereinbelow, the tester-specific polynucleotide can be amplified (concentrated) and isolated more simply (amplifying method of the present invention 3).

Namely, after performing the above step (1) and step (2), the double-stranded tester-specific polynucleotide can be obtained by amplifying the obtained single-stranded polynucleotide and the complementary strand thereof [step (3')]. Subsequently, the non-hybridized single-stranded driver polynucleotide coexisting with the amplified double-stranded tester-specific polynucleotide is decomposed and removed by enzymatic treatment to isolate the double-stranded tester-specific polynucleotide [step (4')].

(Procedure 5)

After performing the above steps (1) and (2), the obtained single-stranded tester-specific polynucleotide is used as template, and the complementary strand thereto is synthesized to obtain the double-stranded tester-specific polynucleotide [double strand step]. Subsequently, the non-hybridized single-stranded driver polynucleotide coexisting with the double-stranded tester-specific polynucleotide is decomposed and removed by enzymatic treatment according to the step (4'). In this case, the tester-specific polynucleotide obtained in the step (2) can be easily isolated (obtaining method of the present invention 2).

(Procedure 6)

After performing the above step (1) and step (2) and the isolation step, according to the above double strand step, using the single-stranded tester-specific polynucleotide as template, the complementary strand thereto is synthesized to obtain the double-stranded tester-specific polynucleotide (amplifying method of the present invention 4).

As the obtaining method of the present invention, the above procedure 1 is preferable. Further, as the amplifying method of the present invention, the above procedures 2 and 3 are preferred, and the procedure 3 is particularly preferred.

The method of the present invention will be specifically explained hereinbelow by exemplifying the case when single-stranded cDNA added with adaptor is used as the tester polynucleotide and the double-stranded cDNA is used as the driver polynucleotide.

[Preparation of Single-Stranded Tester cDNA]

Two types of primer consisting of the 5'-terminal phosphorylated primer designed by the known sequence derived from vectors of cDNA insertion fragment in both side, and the non-phosphorylated primer having different sequence therefrom in the cDNA library prepared by using mRNA extracted from the objective sample as the template by known method or commercially available cDNA library, are prepared. Using the prepared two types of primer and the cDNA library as the template, double-stranded cDNA, to which adaptor sequence is added to 5'-terminal and 3'-terminal, derived from the tester gene is amplified by PCR, etc. Alternatively, mRNA is extracted from the objective sample by known method. Two types of primer consisting of the 5'-terminal phosphorylated primer designed by the known sequence and the non-phosphorylated primer having different sequence therefrom, are prepared. Using the extracted mRNA as the template, cDNA, to which adaptor sequence is added to 5'-terminal and 3'-terminal, is prepared according to the oligo capping method by using the two types of primer prepared. Then the primers are prepared based on the adaptor sequence at 5'-terminal and 3'-terminal, and the double-stranded cDNA is amplified by PCR, etc.

If necessary, the amplified double-stranded cDNA added with adaptor is subjected to extraction treatment with phenol/chloroform/isoamyl alcohol mixture and alcohol precipitation treatment.

The amplified double-stranded cDNA added with adaptor is treated with enzyme, which removes 5'-terminal phosphorylated DNA strand of the double-stranded DNA, such as lambda exonuclease, then, reaction of the enzyme is terminated, for example, by treating with a reaction terminator, for example, a chelating agent such as EDTA and/or heat treatment, and cDNA strand at the side of 5'-terminal phosphorylated primer is removed to obtain the single-stranded tester cDNA bound (added) with the adaptor.

Further, if necessary, the thus obtained single-stranded tester cDNA is purified by means of column purification.

Figure 2:
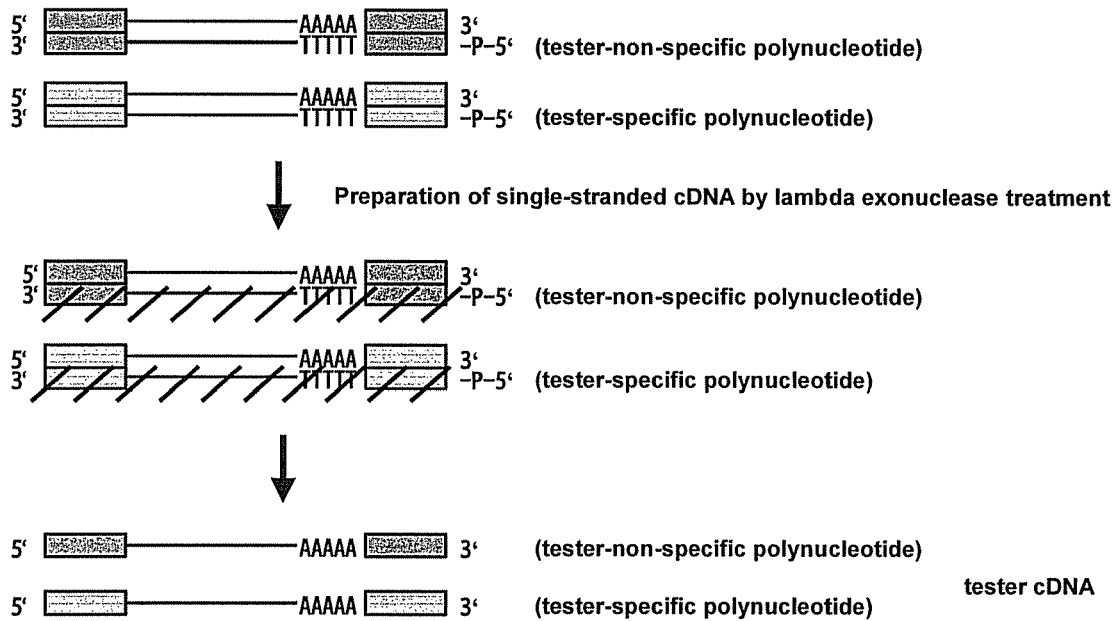
FIG. 2 is a schematic drawing of the preparation step of single-stranded tester cDNA of the present invention.

Outline of the above method is illustrated in FIG. 2.

(Preparation of Double-Stranded Driver cDNA)

Two types of primer having different sequence designed by the known sequence derived from vectors of cDNA insertion fragment in both side in the cDNA library prepared by using mRNA extracted from other different sample from the objective sample as the template by known method or commercially available cDNA library are prepared. Using the prepared two types of primer and the cDNA library as the template, double-stranded cDNA, to which adaptor sequence is added to 5'-terminal and 3'-terminal, derived from the driver gene is amplified by PCR, etc.

If necessary, the amplified double-stranded cDNA added with adaptor is subjected to extraction treatment with phenol/chloroform/isoamyl alcohol mixture and alcohol precipitation treatment.

In the amplified double-stranded cDNA added with adaptor, from both side of insertion fragment cDNA to the amplified primer (adaptor) is cleaved by utilizing multi-cloning site in both side of the insertion fragment to obtain the double-stranded driver cDNA consisting of insertion fragment alone [adaptor non-added double-stranded driver cDNA].

Further, if necessary, the thus obtained double-stranded driver cDNA is purified by means of column purification, etc.

Figure 3:
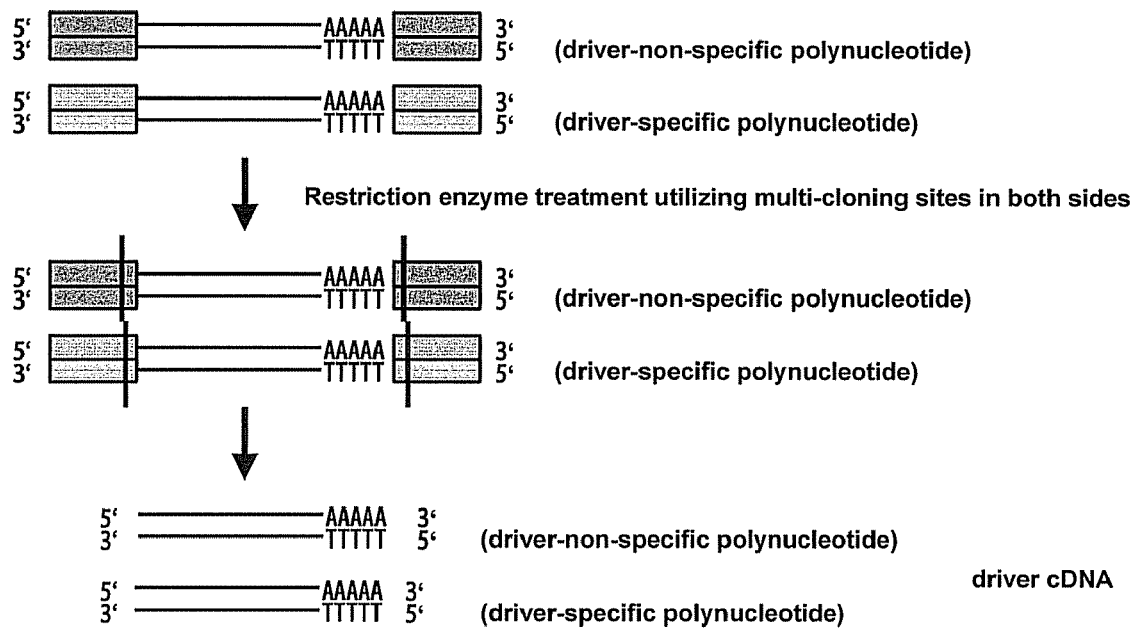
FIG. 3 is a schematic drawing of the preparation step of double-stranded driver cDNA of the present invention.

Outline of the above method is illustrated in FIG. 3.

[Hybridization of Tester cDNA and Driver cDNA: Step (1)]

The prepared single-stranded tester cDNA and an excess amount of the double-stranded driver cDNA to the single-stranded tester cDNA are added and mixed in buffer solution containing a suitable amount of sodium salt, and thermal denaturation is performed by heating at suitable temperature for suitable time. Subsequently, hybridization is performed at suitable temperature for suitable time to generate hybridized double-stranded cDNA of the tester cDNA and the driver cDNA complementary thereto to obtain the hybridization solution containing a single-stranded tester-specific cDNA, a double-stranded hybrid with the single-stranded tester-non-specific cDNA and the single-stranded driver cDNA complementary thereto, an annealed double-stranded driver-specific cDNA, an annealed double-stranded driver-non-specific cDNA, unannealed single-stranded driver-specific cDNA (two types of sense strand and antisense strand) and unannealed single-stranded driver non-specific cDNA (two types of sense strand and antisense strand).

Figure 4:
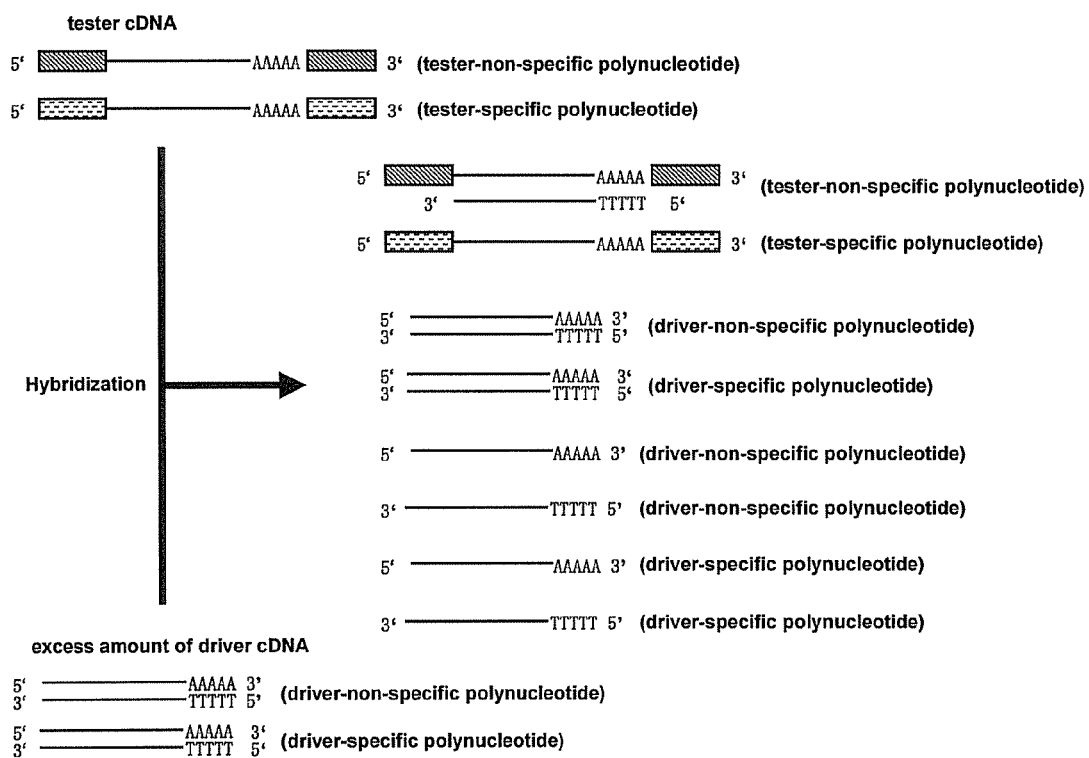
FIG. 4 is a schematic drawing of the hybridization step [step (1)] of the tester cDNA and the driver cDNA of the present invention.

Outline of the method described above is illustrated in FIG. 4.

[Removal of Hybridized Double-Stranded cDNA: Step (2)]

To the obtained hybridization solution, a solution containing deoxyribonuclease having a property of dominantly decomposing double-strand DNA such as double-strand specific DNA nuclease and a solution containing activator and stabilizer are added and mixed, and treated (reacted) generally at 20° C. to 80° C., preferably at 30° C. to 75° C., and more preferably at 50° C. to 70° C., generally at pH 6 to 9, preferable at pH 6.5 to 8.5, and more preferably at pH 7 to 8, and generally for 0.5 min. to 60 min., preferably for 1 min. to 45 min., and more preferably 5 min. to 30 min., to decompose hybridized double-stranded cDNA (double-stranded hybrid with single-stranded tester non-specific cDNA and single-stranded driver cDNA complementary thereto, annealed double-stranded driver-specific cDNA and annealed double-stranded driver-non-specific cDNA) contained in the hybridization solution. Thereafter, the deoxyribonuclease reaction is terminated by performing, for example, treatment with a reaction terminator, for example, a chelating agent such as EDTA, or treatment with the reaction terminator, and the heat treatment to obtain the reaction mixture containing single-stranded tester-specific cDNA, unannealed single-stranded driver-specific cDNA (two types of sense strand and antisense strand) and unannealed single-stranded driver-non-specific cDNA.

Further, if necessary, the cDNA is subjected to extraction treatment with phenol/chloroform/isoamyl alcohol mixture and treatment with alcohol precipitation.

Figure 5:
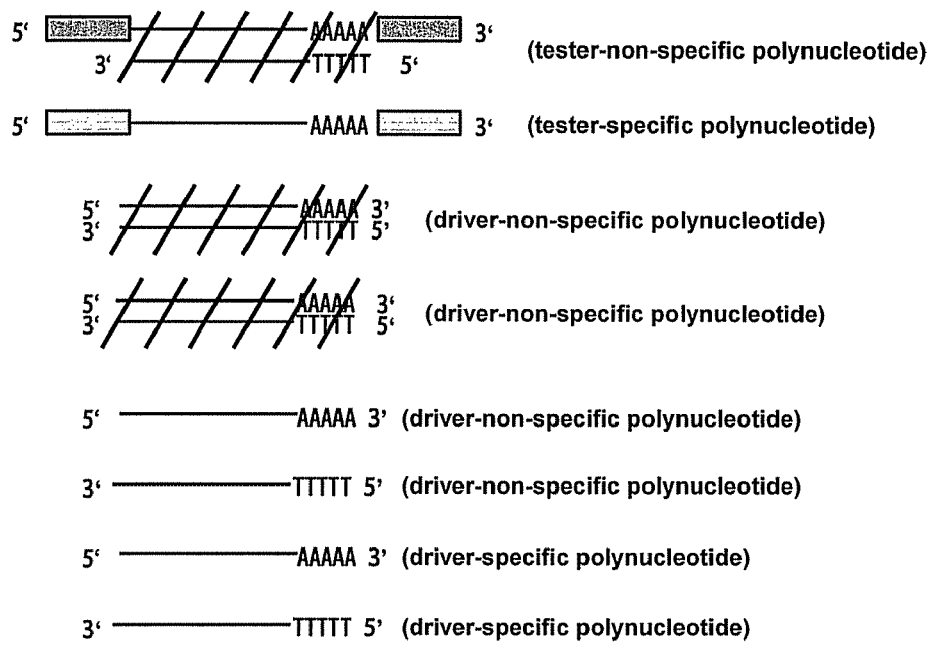
FIG. 5 is a schematic drawing of the removal step [step (2)] of hybridized double-stranded cDNA of the present invention.

Outline of the method described above is illustrated in FIG. 5.

[Amplification of Non-Hybridized Single-Stranded Tester-Specific cDNA: Step (3)]

To the thus obtained reaction mixture, two types of primer having same sequence as used in the preparation of single-stranded tester cDNA described hereinabove (proviso that every 5'-terminal is not phosphorylated), deoxyribonucleotide triphosphate (dATP, dCTP, dGTP and dTTP), for example, polymerase such as Taq DNA polymerase, and an appropriate amount of buffer solution for PCR are added. (a) The obtained solution is heated at suitable temperature for suitable time to perform thermal denaturation treatment. Subsequently, (b) the primer is annealed to the single-stranded tester-specific cDNA (2nd cycle or later: single-stranded tester-specific cDNA and amplified complementary strand thereof) by cooling the solution. Thereafter, (c) the solution is treated at suitable temperature for suitable time, and the primer is extended by an action of the polymerase to synthesize (amplify) the complementary strand to the single-stranded tester-specific cDNA (2nd cycle or later: the complementary strand to the single-stranded tester-specific cDNA and the amplified complementary strand to the complementary strand to the single-stranded tester-specific cDNA). The non-hybridized single-stranded tester-specific cDNA and the complementary strand thereof are amplified by repeating the steps (a) to (c) for suitable number of times to obtain the reaction mixture containing the amplified double-stranded tester-specific cDNA, the single-stranded driver-specific cDNA (two types of sense strand and antisense strand) and the single-stranded driver-non-specific cDNA (two types of sense strand and antisense strand).

Further, if necessary, the cDNA is subjected to extraction treatment with phenol/chloroform/isoamyl alcohol mixture and treatment with alcohol precipitation.

Outline of the method described above is illustrated in FIG. 6.

[Removal of Non-Hybridized Single-Stranded cDNA: Step (4)]

To the obtained reaction mixture, a solution containing deoxyribonuclease having a property of not decomposing double-stranded DNA and dominantly decomposing single-strand DNA such as the single-strand specific DNA nuclease and a solution containing activator and stabilizer are added and mixed, and treated (reacted) generally at 20° C. to 60° C., preferably at 25° C. to 50° C., and more preferably at 30° C. to 40° C., generally at pH 7 to 11, preferable at pH 8 to 10.5, and more preferably at pH 9 to 10, and generally for 0.1 min. to 60 min., preferably for 0.5 min. to 45 min., and more preferably 1 min. to 30 min., to decompose single-stranded driver cDNA (single-stranded driver-specific cDNA (two types of sense strand and antisense strand) and single-stranded driver-non-specific cDNA (two types of sense strand and antisense strand)). Thereafter, the deoxyribonuclease reaction is terminated by performing, for example, treatment with a reaction terminator, for example, a chelating agent such as EDTA and/or heat treatment.

Further, if necessary, the obtained double-stranded tester-specific cDNA is subjected to purification with column.

Figure 7:
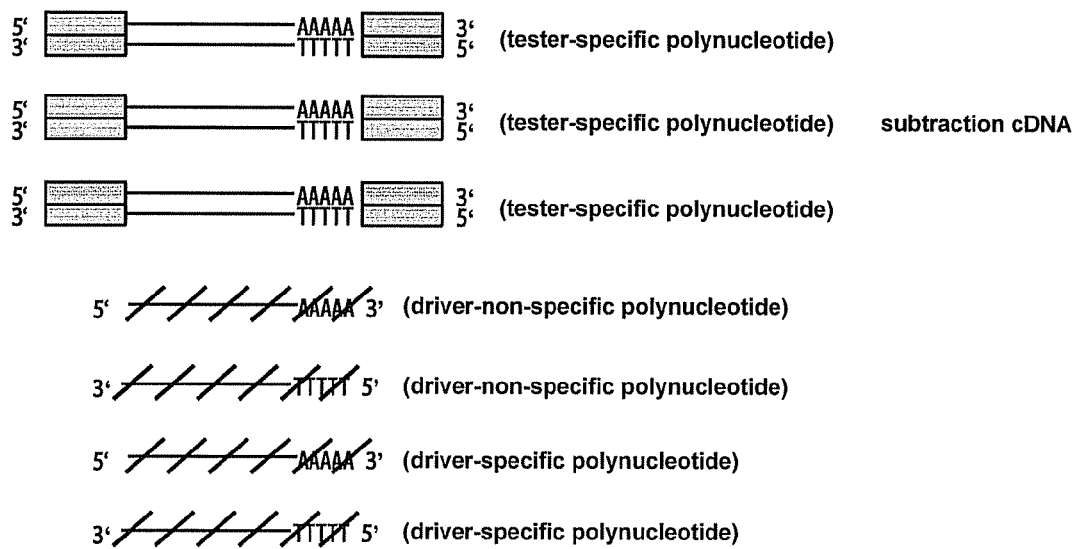
FIG. 7 is a schematic drawing of the removal step [step (4)] of non-hybridized single-stranded driver cDNA of the present invention.

Outline of the method described above is illustrated in FIG. 7.

2-4. Identification Method for Gene Mutation of the Present Invention

The tester-specific polynucleotide obtained, amplified or isolated by the method of the present invention is used in various identification and screening means such as identification of gene mutation in the tester, for example, as follows.

(1) Identification of base sequence of gene mutation or identification of novel gene sequence can be made by determining the base sequence of the tester-specific polynucleotide using the known base sequencing method.

(2) Identification whether the mutant gene is pathogenic or not

Whether a specific mutant gene (mRNA) is pathogenic or not can be identified by confirming and comparing expression of the specific mutant gene (mRNA) in the tester (derived from abnormal (diseased) sample) and the driver (derived from normal (healthy subject) sample) by using Northern blotting, RT-PCR, real-time PCR, etc.

(3) Identification of position on genomic DNA of mutant gene

In the genome map of the total DNA sequence of animal such as human, mouse, rat, etc., position of mutant gene on genomic DNA can be identified by comparing with the total DNA sequence and base sequence of the mutant gene using database. Further, in the case when total DNA sequence is not mapped, position of mutant gene on genomic DNA can be identified, for example, by a known method such as FISH method.

(4) Diagnostic determination, prediction and prevention of disease

Whether a specific mutant gene (mRNA) is pathogenic or not can be identified by confirming and comparing expression of the specific mutant gene (mRNA) in the tester (derived from abnormal (diseased) sample) and the driver (derived from normal (healthy) sample) by using, for example, Northern blotting, RT-PCR, real-time PCR, etc.

(5) Identification of therapeutic effect and identification of treatment time of disease Whether the specific mutant gene (mRNA) is pathogenic or not can be identified by confirming and comparing expression of the specific mutant gene (mRNA) in the tester (derived from abnormal (diseased) sample) and the driver (derived from normal (healthy) sample) by using, for example, Northern blotting, RT-PCR, real-time PCR, etc.

(6) By performing screening of cDNA library, EST library, etc. using the tester-specific polynucleotide as a probe, mutant gene involved in a certain function or phenotypic expression can be screened. Such method includes the known screening methods (Beck M T, Holle L, Chen W Y. Biotechniques. 2001 October; 31 (4):782-4, 786), for example, such method that the tester-specific polynucleotide labeled with labeling substance or oligonucleotide containing a part of or total complementary strand thereof is used as a probe, and the hybridization is performed with the above library immobilized on the DNA chip.

(7) The tester-specific polynucleotide (in particular, genomic DNA or cDNA) is cloned to prepare subtractive genomic DNA or cDNA library. Hybridization is performed by using genomic DNA or cDNA extracted from normal (healthy) sample and genomic DNA or mRNA group extracted from abnormal (diseased) sample as a probe, thereby genomic DNA or cDNA reacted with only the genomic DNA or mRNA group of the abnormal (diseased) sample has a possibility to be unknown pathogenic origin. Namely, according to such method, there is a possibility that unknown pathogen can be detected.

(8) The tester-specific polynucleotide (in particular, cDNA) is inserted into the suitable vector such as plasmid vector, and E. coli, etc. is transformed by using such vector to practice cloning the tester-specific gene.

(9) Base sequence of the tester-specific polynucleotide (in particular, cDNA) or cloned DNA is determined, and the primer designed based on such base sequence is used to perform 3' and 5' RACE to obtain full-length cDNA of the mutant gene.

(10) TAIL-PCR using the primer is performed, or screening of genomic library using the tester-specific polynucleotide as a probe is performed, and as a result, the specifically acting promoter (promoter of the mutant gene) in certain function or phenotypic expression can be screened.

(11) High-throughput identification of specifically expressed gene

Micro array (chip) is prepared by using the tester-specific polynucleotide (in particular, cDNA) obtained by the method of the present invention, and using such micro array, identification and analysis of the above steps (1) to (7) can rapidly and simply be performed.

Consequently, the method of the present invention includes various methods of identification and screening methods as described hereinabove using the tester-specific polynucleotide obtained, amplified or isolated by the method of the present invention. In addition, the identification method and the screening method may be performed by the known methods except that the tester-specific polynucleotide obtained, amplified or isolated by the method of the present invention is used, and reagents to be used therein are also the same as used in the known method.

Consequently, in the identification method for gene mutation of the present invention, the method including at least one step selected from (1) to (9) hereinbelow is preferable.

(1) A step of determining base sequence of obtained tester-specific polynucleotide.

(2) A step of confirming expression level of the obtained tester-specific polynucleotide (specific mutant gene; mRNA) in the tester and the driver, and comparing thereof by Northern blotting, RT-PCR, real-time PCR, etc.

(3) A step of identifying the position of obtained tester specific polynucleotide (mutant gene) on the genomic DNA by comparing total DNA sequence and the obtained base sequence of the tester-specific polynucleotide (mutant gene), or a step of identifying the position of obtained tester specific polynucleotide (mutant gene) on the genomic DNA by a known method such as FISH method, etc.

(4) A step of performing screening cDNA library, EST library, etc. by using the obtained tester-specific polynucleotide as a probe.

(5) A step of performing cloning the obtained tester-specific polynucleotide (in particular, genomic DNA or cDNA) to prepare subtractive genomic DNA or cDNA library, and hybridizing the genomic DNA or cDNA extracted from the normal (healthy) sample and the genomic DNA or mRNA group extracted from the abnormal (diseased) sample as a probe.

(6) A step of performing cloning the tester-specific gene by inserting the obtained tester-specific polynucleotide (in particular, cDNA) into a suitable vector such as plasmid vector, and transforming E. coli, etc. by using the vector.

(7) A step of obtaining full-length cDNA of the mutant gene by using the obtained tester-specific polynucleotide as a probe or primer.

(8) A step of performing TAIL-PCR using the obtained tester-specific polynucleotide as a primer, or performing screening the genomic library using the obtained tester-specific polynucleotide as a probe, and performing screening the promoter specifically acting in certain function or phenotypic expression (promoter of mutant gene).

(9) A step of preparing micro array (chip) using the obtained tester-specific polynucleotide (in particular, cDNA), and performing the above steps (1) to (7) using the same.

Further, the present invention includes a probe or a primer consisting of the tester-specific polynucleotide obtained, amplified or isolated by the method of the present invention, or a probe or a primer consisting of the oligonucleotide containing a part of or entire of the complementary strand thereof, and cDNA library which can be obtained by the method of the present invention.

3. Kit of the Present Invention

Kit of the present invention is used for performing the obtaining method, amplifying method or identifying method of the present invention as described above.

Such kit comprises, a) at least an enzyme having a property of not decomposing the single-stranded polynucleotide but dominantly decomposing a hybridized double-stranded polynucleotide, to be used for removing the hybridized double-stranded polynucleotide (i.e. the double-stranded polynucleotide of the tester-non-specific polynucleotide and the driver polynucleotide complementary thereto) in the step (2) of the present invention as described hereinabove, preferably deoxyribonuclease having a property of dominantly decomposing the double-stranded DNA, more preferably double-strand specific DNA nuclease;

b) preferably further an enzyme having a property of removing the nucleic acid strand of the half side of double-stranded polynucleotide to prepare single-stranded polynucleotide to be used for preparing the single-stranded polynucleotide from the double-stranded polynucleotide derived from the tester prepared in the step (1') of the present invention as described hereinbefore, or enzyme group which can prepare the single-stranded polynucleotide by removing the nucleic acid strand of the half side of the double-stranded polynucleotide by combining two or more kinds of enzymes, preferably an enzyme having a property of preparing the single-stranded polynucleotide by removing the nucleic acid strand of the half side of the double-stranded polynucleotide, more preferably lambda exonuclease; and c) an enzyme having a property of not decomposing the double-stranded polynucleotide but decomposing dominantly the single-stranded polynucleotide to be used for specifically decomposing the single-stranded polynucleotide (single-stranded driver polynucleotide) coexisting with the double-stranded tester-specific polynucleotide in the step (4) of the present invention as described hereinbefore, preferably deoxyribonuclease having a property of not decomposing the double-stranded DNA but decomposing dominantly the single-stranded DNA, more preferably the single-strand specific DNA nuclease, further more specifically exonuclease I.

Preferable aspects and specific examples of these component requirements are as described above.

Further, the kit of the present invention can be prepared by adding reagents other than the above. Examples of such reagents are, for example, at least one selected from the following a) to j), but not limited thereto.

a) Buffer solution for an enzyme having a property of not decomposing the single-stranded polynucleotide but dominantly decomposing the hybridized double-stranded polynucleotide (e.g. Good's buffer such as HEPES, etc. containing sodium salt, if necessary, magnesium salt and thiol compound);

a') Solution for terminating the reaction of an enzyme having a property of not decomposing the single-stranded polynucleotide but dominantly decomposing the hybridized double-stranded polynucleotide (e.g. for example, water and buffers as described above containing reaction terminator such as chelating agent);

b) Buffer solution for an enzyme having a property of preparing the single-stranded polynucleotide by removing the nucleic acid strand of the half side of the double-stranded polynucleotide or enzyme group which can prepare the single-stranded polynucleotide by removing the nucleic acid strand of the half side of the double-stranded polynucleotide by combining two or more kinds of enzymes (e.g. buffer solution such as glycine containing magnesium salt and surfactant, etc.);

c) Buffer solution for an enzyme having a property of not decomposing the double-stranded polynucleotide but decomposing dominantly the single-stranded polynucleotide (e.g. buffer solution such as glycine containing magnesium salt and thiol compound, etc.);

d) Buffer solution for hybridization (e.g. Good's buffer containing sodium salt, etc.);

e) Reagent for extracting polynucleotide (e.g. buffer solution for pulverization, phenol, chloroform, SDS, β-mercaptoethanol, etc.);

f) Reagent for PCR (e.g. polymerase, buffer solution for polymerase, one or more types of primers, nucleotide mixture, etc.);

g) Reagent for electrophoresis (agarose or polyacrylamide gel, loading buffer solution, reagent for ethidium bromide staining, etc.);

h) Reagents for isolation (separation) or purification of polynucleotide to be used for removing excess primer after PCR, removing short chain DNA amplified by mis-annealing, removing short DNA without digesting completely by nuclease, etc. (e.g. column for purification); and i) Reagent for alcohol precipitation (e.g. ethanol solution, isopropanol solution, polymer carrier, sodium acetate solution, etc.).

Further, an instruction manual for use in obtaining, amplifying and identifying method of the present invention as described hereinbefore may be contained. The "instruction manual" means an instruction (operating) manual, appended paper (package insert) or pamphlet (leaflet), etc. for the kit, in which features, principles, operation procedures, etc. in the method of the present invention are practically described by writing or illustrations.

The method of the present invention exhibits effect as follows.

(1) The tester polynucleotide and the driver polynucleotide can be prepared from cDNA library.

In the conventional methods, since circular plasmid could not be removed during the step for preparing subtraction cDNA, the tester polynucleotide and the driver polynucleotide could only be prepared from cDNA, and consequently, there was a problem of troublesome procedure for preparation of cDNA and a limited amount of prepared cDNA. On the other hand, since the double-stranded polynucleotide can be removed by enzymatic treatment using the enzyme having a property of not decomposing the single-stranded polynucleotide but decomposing dominantly the hybridized double-stranded polynucleotide in the step (2) of the method of the present invention, both of the tester polynucleotide and the driver polynucleotide can be prepared from the cDNA library (plasmid vector).

(2) Only one time of hybridization (subtractive hybridization) is required.

In the conventional method, since the tester polynucleotide is double stranded, the annealed double strand hybrid occurs between the tester polynucleotides, and as a result, even though excess amount of driver polynucleotide is used, highly expressed tester-non-specific polynucleotide (housekeeping gene) is remained, and detrimental effect on the following PCR amplification could occur. For that reason, in the conventional method, hybridization had to be repeated for 2 to 3 or more times. Contrary to that, since the tester polynucleotide is single strand in the present invention, the annealed double-strand hybrid dose not occur between tester polynucleotides, consequently only one time of hybridization is essentially sufficient.

(3) The tester-non-specific polynucleotide can be decomposed and removed from polynucleotides existing in the tester by one time of enzymatic treatment.

In the conventional subtraction method by physical binding or adsorption, since single-stranded polynucleotide and hybridized double-stranded polynucleotide obtained by the result of subtractive hybridization were removed by physical binding or adsorption, these could not strictly be separated in practice and were factors causing lowering of the subtraction efficiency. However, since the hybridized double-stranded polynucleotide is removed by enzymatic treatment in the present invention, the hybridized double-stranded polynucleotide is removed with high efficiency by one enzymatic treatment, thereby the single-stranded tester-specific polynucleotide can be obtained with high efficiency.

(4) Tester-specific polynucleotide can be concentrated easily.

When PCR is performed by using the primer designed and prepared based on the sequence existing in the tester-specific polynucleotide and the sequence not existing in the polynucleotide derived from the driver, the driver polynucleotide can not be amplified and only the tester-specific polynucleotide can be practically amplified, and the tester-specific polynucleotide can be concentrated, then the subtract polynucleotide can be prepared efficiently.

(5) The driver polynucleotide can be easily removed.

The driver polynucleotide coexisting with the tester-specific polynucleotide can be easily removed by the step (4) of the present invention. In particular, in the case when the double-stranded tester-specific polynucleotide is coexisting with the single-stranded driver polynucleotide, the single-stranded driver polynucleotide can easily be removed by enzymatic treatment. As a result, since density of the tester-specific polynucleotide can be further increased, influence of contamination (remaining) of the driver polynucleotide, which was a problem in the conventional method, is further reduced, and highly efficient subtraction polynucleotide can be prepared.

Hereinafter, the present invention will be explained in detail by referring to Example and Comparative Example, however, the present invention is not limited thereto in any way.

Example (1) Extraction of Total RNA from Hep G2 Cell Derived from Human Liver Cancer Using ISOGEN (Nippon Gene Co., Ltd.), total RNA was extracted from Hep G2 cells (Health Science Research Resources Bank) according to the instruction manual.

Hep G2 cells were cultured in four 225 mL culture flasks (Nalge Nunc International K.K.) to $5 \times 10^6$ cells/cm$^2$, and washed with phosphate buffer (pH 7.5). ISOGEN (Nippon Gene Co., Ltd.) 15 mL/one cultured flask was added thereto to detach (peel) cells and cells were transferred to the centrifugal tube (Nalge Nunc International K.K., Oak Ridge Centrifuge Tube, 50 mL). Chloroform 3 ml was added thereto, the mixture was stirred and centrifuged with high-speed centrifuge (Hitachi Ltd., SCR20B) at 12,000 rpm, at 4° C. for 15 minutes and 10 mL each of the supernatant was recovered. The supernatant was transferred to new centrifugal tube, stirred with addition of isopropanol 10 mL (Wako Pure Chemical Industries Ltd.), and centrifuged with high-speed centrifuge (Hitachi Ltd., SCR20B) at 12,000 rpm, at 4° C. for 15 minutes. The supernatant was removed off and the precipitate was washed with 70% ethanol (Wako Pure Chemical Industries Ltd.), dried, dissolved in sterile water and measured the RNA concentration by using spectrophotometer (Beckmann Coulter Inc., DU640) at UV 260 nm. After measuring the concentration, RNA solution 250 µL (500 µg) prepared to 2 µg/µL with sterile water was obtained.

(2) Extraction of Poly(A)$^+$ RNA from Total RNA Derived from Hep G2 Cells

Using Hep G2 cells total RNA 500 µg obtained in the above (1) and using Oligotex-dT 30 Super (Takara Biotech Co., Ltd.), Poly(A)$^+$ RNA was extracted according to the instruction manual.

To HepG2 cells total RNA solution 250 µL, 2× Elution Buffer (20 mM Tris-HCl buffer containing 2 mM EDTA and 0.2% SDS, pH 7.5) 250 µL were added and mixed. Subsequently, Oligotex-dT 30 Super was added thereto, mixed, and the mixture was heated at 65° C. for 5 minutes, then rapidly cooled in the ice. 5 M sodium chloride 100 µL was added thereto, the mixture was incubated at 37° C. for 10 minutes, and centrifuged with high-speed microcentrifuge (Hitachi Ltd., CF16RX) at 14,500 rpm, at room temperature for 5 minutes. The supernatant was removed off, added sterile water 400 µL, mixed, and the mixture was heated at 65° C. for 5 minutes, then centrifuged with high-speed microcentrifuge (Hitachi Ltd., CF16RX) at 14,500 rpm, at room temperature for 5 minutes. The supernatant was recovered, added 5 M sodium chloride 20 µL and ethanol 1 mL, mixed, and the mixture was centrifuged with high-speed microcentrifuge (Hitachi Ltd., CF16RX) at 14,500 rpm, at 4° C. for 10 minutes. The supernatant was removed off, washed with 70% ethanol, dried, dissolved in sterile water, and the RNA concentration in the mixture was measured by using spectrophotometer (Beckmann Coulter Inc., DU640) at UV 260 nm. After measuring the concentration, RNA solution 28 µL (7 µg) prepared to 0.25 µg/µL with sterile water was obtained.

(3) Preparation of cDNA Library of Hep G2 Cells

Poly(A)$^+$ RNA 5 µg derived from Hep G2 cells obtained in the above (2) was taken to prepare cDNA library of Hep G2 cells according to the instruction manual using Time Saver cDNA Synthesis Kit (Amersham plc). Vector used was pNEB 193 (New England Biolabs Inc.). DH5α was used for transformation. Further, plasmid library was cultured in 100 ml of Luria-Bertani' broth (containing ampicillin sodium 100 µg/ml) and thereafter recovered.

To the First-Strand Reaction Mixes (Amersham plc), Hep G2 Poly(A)$^+$ RNA 5 µg (20 µL) obtained in the above (2), which was heated at 65° C. for 10 minutes and thereafter immediately cooled in ice, Oligo-dT (24)-Pac I site Primer (5'-TTTTTTTAAT-TAATTTTTTTTTTTTTTTTTTTTTTTT-3', Sigma Genosys Inc., 0.5 mg/ml) 1 µL and DTT solution (Amersham plc) 1 µL were mixed, and the mixture was incubated at 37° C. for 1 hour to perform first strand reaction (reverse transcription reaction). To the Second-Strand Reaction Mixes (Amersham plc), the first strand reaction mixture was mixed and the mixture was incubated at 12° C. for 30 minutes, then incubated at 22° C. for 1 hour to perform the second strand reaction.

Subsequently, the second strand reaction was terminated by heating at 65° C. for 10 minutes, and removed the primer and low molecular weight DNA was removed by using SizeSep 400 Spun Columns (Amersham plc) to obtain double-stranded cDNA.

To the prepared double-stranded cDNA 100 µL, EcoR I/Not I adaptor (Amersham plc) 5 µL, PEG Buffer (Amersham plc) 30 µL, ATP Solution (Amersham plc, 15 mM) 1 µL, and T4 DNA Ligase (5 units) (Amersham plc) 1 µL were added, the mixture was incubated at 16° C. for 1 hour, and heated at 65° C. for 10 minutes to denature T4 DNA Ligase. To the obtained reaction mixture (solution containing cDNA bound with adaptor) 137 µL, mixture of phenol:chloroform: isoamyl alcohol (25:24:1) (Nippon Gene Co., Ltd.) 140 µL was added, the mixture was stirred and centrifuged at 14,500 rpm, at room temperature for 3 minutes by using high-speed microcentrifuge (Hitachi Ltd., CF16RX). The supernatant was recovered, and Ethachinmate (Nippon Gene Co., Ltd.) 1 µL, 5M NaCl (Wako Pure Chemicals Industries Ltd.) 7 µL and ethanol (Wako Pure Chemicals Industries Ltd.) 350 µL were added thereto, mixed and the mixture was centrifuged at 14,500 rpm, at 4° C. for 10 minutes by using high-speed microcentrifuge (Hitachi Ltd., CF16RX). The supernatant was removed off, washed with 70% ethanol (Wako Pure Chemicals Industries Ltd.), dried and dissolved in sterile water 85 µL. To the cDNA dissolved in sterile water, 10×NEB buffer 1 (New England Biolabs Inc.) 10 µL, BSA solution (New England Biolabs Inc.) 1 µL and Pac I (New England Biolabs Inc., 10 units/µL) 4 µL were added, mixed, the mixture was incubated at 37° C. for 2 hours, and heated at 65° C. for 20 minutes to denature Pac I.

The obtained reaction mixture (solution containing cDNA cleaved with Pac I) was treated with Size Sep 400 Spun Columns (Amersham plc), and unbound adaptor and low molecular weight DNA were removed, then obtained solution was adjusted to total amount 150 µL by adding sterile water. Accordingly, cDNA having cleavage end of EcoR I at 5'-terminal and Pac I at 3'-terminal was obtained.

The obtained cDNA 3 µL (about 100 ng reduced to Poly (A)+ RNA), pNEB 193 DNA (New England Biolabs Inc.) 100 ng (2 µL) prepared by cleaving with EcoR I (Nippon Gene Co., Ltd.) and Pac I (New England Biolabs Inc.), and DNA Ligation Kit Ver. 2.1 (Takara Biotech Co., Ltd.) I solution (reaction buffer) 5 µL were mixed, the mixture was incubated at 16° C. for 1 hour, and total amount thereof (10 µL) was transformed into DH5α (100 µL) with heat shock at 42° C. for 30 seconds. The transformed cDNA library was cultured in Luria-Bertani's broth (containing ampicillin sodium 100 µg/ml) 100 ml at 37° C. for 16 hours, and Hep G2 cell plasmid cDNA library inserted to one direction was recovered.

A part of the obtained cDNA library was prepared with sterile water to 10 ng/µL for use as a template for PCR amplification reaction in (4) preparation of tester cDNA hereinbelow.

(4) Preparation of Tester cDNA

The cDNA library of HepG2 cells derived from human liver cancer prepared in the above (3) was used as a template, and the insertion fragment cDNA was amplified by PCR using TOPOTAQ DNA Polymerase (Fidelity Systems Inc.).

Reagents hereinbelow described were mixed and the mixed solution 20 µL was dispensed into 5 tubes of 0.2 mL PCR tube.

cDNA library solution of HepG2 cells derived from human liver cancer: 1 µL (10 ng)
2× Amplification Buffer (Fidelity Systems Inc.) containing 6 mM MgCl$_2$: 50 µL
dNTPs solution (containing each dNTP 10 mM, Amersham plc): 5 µL
M13/pUC Forward Primer solution: 5 µL Phosphorylated primer (5'-P—CCAGTCACGACGTTG-TAAAACG-3') (Sigma Genosys Inc.) was dissolved to give 10 µM in sterile water.

M13/pUC Reverse Primer solution: 5 µL

Non-phosphorylated primer (5'-CACACAGGAAACAGC-TATGACC-3') (Sigma Genosys Inc.) was dissolved to give 10 M in sterile water.

TOPOTAQ DNA Polymerase solution: 4 µL

To TOPOTAQ DNA Polymerase (Fidelity Systems Inc., 3 units/µL) 1 µL, 1× Dilution buffer (Fidelity Systems Inc.) 3 µL was added and mixed to prepare 4 µL.

Sterile water: 30 µL

Subsequently, the mixture was subjected to PCR at 95° C. for 2 minutes, 95° C. for 20 seconds→60° C. for 20 seconds→72° C. for 2 minutes with 30 cycles, and 72° C. for 5 minutes, using Thermal Cycler (MJ Research Inc., PTC-225).

The obtained PCR amplified product (100 µL) was transferred into the 0.6 mL microtube, and equivalent amount (100 µL) of mixture of phenol:chloroform:isoamyl alcohol (25:24: 1) (Nippon Gene Co., Ltd.) was added thereto and mixed.

The mixture was centrifuged at 14,500 rpm, at room temperature for 3 minutes using high-speed microcentrifuge (Hitachi Ltd., CF16RX), and the aqueous phase (supernatant) was transferred into the 0.6 mL microtube. Ethachinmate (Nippon Gene Co., Ltd.) 1 µL, 5M NaCl (Wako Pure Chemicals Industries Ltd.) 5 µL and ethanol (Wako Pure Chemicals Industries Ltd.) 250 µL were added thereto and mixed.

After centrifuged at 14,500 rpm, at room temperature for 5 minutes by using high-speed microcentrifuge (Hitachi Ltd., CF16RX), the supernatant was removed off, and the obtained precipitate was washed with 70% ethanol (Wako Pure Chemicals Industries Ltd.), dried and dissolved in sterile water 44 µL.

Subsequently, 10× Lambda Exonuclease Buffer (EPICENTRE Inc., 670 mM glycine-KOH buffer containing 25 mM magnesium chloride and 0.1% Triton-X100, pH9.4) 5 µL and Lambda Exonuclease (EPICENTRE Inc., 10 units/µL) 1 µL were added to the solution, mixed and the mixture was incubated at 37° C. for 30 minutes. Subsequently, further the mixture was incubated at 80° C. for 15 minutes to denature Lambda Exonuclease.

Sterile water 50 µL was added thereto, to give total volume of 100 µL, then the mixture was centrifuged at 700×g, at room temperature for 5 minutes using CHROMA SPIN+TE-400 Columns (Clontech Inc.), and using low-speed centrifuge (TOMY Co. Lt., LX-120), and low molecular weight DNA and PCR primer were removed. DNA concentration in a part of the mixture was measured at UV 260 nm by using spectrophotometer (Beckman, DU640), and the mixture was diluted with sterile water to give DNA concentration 1 ng/µL using the following equation.

DNA concentration(µg/µL)=OD$_{260}$×37 µg/mL×(dilution rate)/1000

(5) Preparation of Driver cDNA

Insertion fragment cDNA was amplified by PCR using the cDNA library derived from human normal liver tissue (BioChain Inc., cDNA Library: Human Adult Normal Tissue: Liver).

The same reagents as in the above (4) were used except that a solution of cDNA library derived from human normal liver tissue (BioChain Inc., cDNA Library: Human Adult Normal Tissue: Liver) 1 µL (10 ng) was used.

Each reagent was mixed, and the mixture 20 µL was dispensed into five 0.2 mL PCR tubes.

Subsequently, the mixture was subjected to PCR at 95° C. for 2 minutes, 95° C. for 20 seconds→60° C. for 20 seconds→72° C. for 2 minutes with 30 cycles, and 72° C. for 5 minutes, using Thermal Cycler (MJ Research Inc., PTC-225).

The obtained PCR amplified product (100 µL) was transferred into the 0.6 mL microtube, and equivalent amount (100 µL) of mixture of phenol:chloroform:isoamyl alcohol (25:24: 1) (Nippon Gene Co., Ltd.) was added thereto and mixed.

The mixture was centrifuged at 14,500 rpm, at room temperature for 3 minutes by using high-speed microcentrifuge (Hitachi Ltd., CF16RX), and the aqueous phase (supernatant) was transferred into the 0.6 mL microtube. Ethachinmate (Nippon Gene Co., Ltd.) 1 µL, 5M NaCl (Wako Pure Chemicals Industries Ltd.) 5 µL and ethanol (Wako Pure Chemicals Industries Ltd.) 250 µL were added thereto and mixed.

After centrifuged at 14,500 rpm, at room temperature for 5 minutes by using high-speed microcentrifuge (Hitachi Ltd., CF16RX), the supernatant was removed off, and the obtained precipitate was washed with 70% ethanol (Wako Pure Chemicals Industries Ltd.), dried and dissolved in sterile water 10 µL.

The obtained PCR amplified product 5 µg was adjusted with sterile water to give total volume 43 µL, and 10×H Buffer (Nippon Gene Co., Ltd.) 5 µL, EcoR I (Nippon Gene Co., Ltd., 10 units/µL) 1 µL and Xho I (Nippon Gene Co., Ltd., 10 units/µL) 1 µL were added thereto, mixed and the mixture was incubated at 37° C. for 2 hours to cleave to the PCR Primer using restriction enzyme of the multicloning site in both side of the insertion fragment. Then the restriction enzyme was denatured by heating at 65° C. for 20 minutes.

Subsequently, sterile water 50 µL was added thereto, to give total volume of 100 µL, then the mixture was centrifuged at 700×g, at room temperature for 5 minutes using CHROMA SPIN+TE-400 Columns (Clontech Inc.), and using low-speed centrifuge (TOMY Co. Lt., LX-120), and low molecular weight DNA and PCR primer were removed. DNA concentration in a part of the mixture was measured at UV 260 nm by using spectrophotometer (Beckman, DU640), and the mixture was diluted with sterile water to give DNA concentration 100 ng/µL using the following equation.

DNA concentration(µg/µL)=$OD_{260}$×50 µg/mL×(dilution rate)/1000

(6) Hybridization

To the solution 3 µL containing the tester cDNA 1 µL (1 ng) prepared in the above (4) and the driver cDNA 2 µL (200 ng) prepared in the above (5), 4× Hybridization Buffer (200 mM HEPES buffer containing 2M NaCl, pH7.3) 1 µL was added, mixed and the heat denaturation was performed at 98° C. for 2 minutes by using Thermal Cycler (MJ Research Inc., PTC-225), and hybridization was performed at 68° C. for 15 hours.

(7) Removal of Hybridized Double-Stranded cDNA by Treatment with Double-Strand Specific DNA Nuclease To the hybridization solution maintained at 68° C., 2×DSN master Buffer (Evrogen, 100 mM Tris-HCl buffer containing 10 mM magnesium chloride and 2 mM DTT, pH 8.0) 5 µL heated at 68° C., was added, mixed and the mixture was incubated at 68° C. for 10 minutes. Double-strand specific DNA nuclease (Duplex-specific nuclease: Evrogen Inc., 1 kunitz-units/µL) 1 µL was added thereto and the mixture was incubated at 68° C. for 30 minutes.

Subsequently, stop solution (5 mM EDTA aqueous solution) 10 µL was added thereto and the mixture was incubated at 68° C. for 5 minutes to terminate Double-strand specific DNA nuclease reaction.

To the obtained reaction mixture, sterile water 80 µL and equivalent amount (100 µL) of mixture of phenol:chloroform:isoamyl alcohol (25:24:1) (Nippon Gene Co., Ltd.) was added and mixed.

The mixture was centrifuged at 14,500 rpm, at room temperature for 3 minutes using high-speed microcentrifuge (Hitachi Ltd., CF16RX), and the aqueous phase (supernatant) was transferred into the 0.6 mL microtube. Ethachinmate (Nippon Gene Co., Ltd.) 1 µL, 5M NaCl (Wako Pure Chemicals Industries Ltd.) 5 µL and ethanol (Wako Pure Chemicals Industries Ltd.) 250 µL were added thereto and mixed. After centrifuged at 14,500 rpm, at room temperature for 5 minutes by using high-speed microcentrifuge (Hitachi Ltd., CF16RX), the supernatant was removed off, and the obtained precipitate was washed with 70% ethanol (Wako Pure Chemicals Industries Ltd.), dried and dissolved in sterile water 31 µL.

(8) PCR Amplification of Non-Hybridized Tester cDNA

Reagents hereinbelow described were mixed and the mixed solution 20 µL was dispensed into 5 tubes of 0.2 mL PCR tube.

Reaction mixture containing single-stranded tester cDNA prepared in the above (7): 31 µL 2× Amplification Buffer (Fidelity Systems Inc.) containing 6 mM $MgCl_2$: 50 µL dNTPs solution (containing each dNTP 10 mM, Amersham plc): 5 µL M13/pUC Forward Primer solution: 5 µL Phosphorylated primer (5'-P—CCAGTCACGACGTTG-TAAAACG-3') (Sigma Genosys Inc.) was dissolved to give 10 µM in sterile water.

M13/pUC Reverse Primer solution: 5 µL

Non-phosphorylated primer (5'-CACACAGGAAACAGC-TATGACC-3') (Sigma Genosys Inc.) was dissolved to give 10 M in sterile water.

TOPOTAQ DNA Polymerase solution: 4 µL

To TOPOTAQ DNA Polymerase (Fidelity Systems Inc., 3 units/µL)

1 µL, 1× Dilution buffer (Fidelity Systems Inc.) 3 µL was added and mixed to prepare 4 µL.

Subsequently, the mixture was subjected to PCR at 95° C. for 2 minutes, 95° C. for 20 seconds→60° C. for 20 seconds→72° C. for 2 minutes with 35 cycles, and 72° C. for 5 minutes, using Thermal Cycler (MJ Research Inc., PTC-225).

The obtained PCR amplified product (100 µL) was transferred into the 0.6 mL microtube, and equivalent amount (100 µL) of mixture of phenol:chloroform:isoamyl alcohol (25:24:1) (Nippon Gene Co., Ltd.) was added thereto and mixed.

The mixture was centrifuged at 14,500 rpm, at room temperature for 3 minutes using high-speed microcentrifuge (Hitachi Ltd., CF16RX), and the aqueous phase (supernatant) was transferred into the 0.6 mL microtube. Ethachinmate (Nippon Gene Co., Ltd.) 1 µL, 5M NaCl (Wako Pure Chemicals Industries Ltd.) 5 µL and ethanol (Wako Pure Chemicals Industries Ltd.) 250 µL were added thereto and mixed.

After centrifuged at 14,500 rpm, at room temperature for 5 minutes by using high-speed microcentrifuge (Hitachi Ltd., CF16RX), the supernatant was removed off, and the obtained precipitate was washed with 70% ethanol (Wako Pure Chemicals Industries Ltd.), dried and dissolved in sterile water 44 µL.

(9) Removal of Non-Hybridized Single-Stranded Driver cDNA by Treatment with Exonuclease I To the PCR amplified product (tester cDNA amplified product) prepared in the above (8) 44 µL, 10× Exonuclease I Buffer (New England Biolabs Inc., 670 mM glycine-KOH buffer containing 67 mM magnesium chloride and 100 mM 2-mercaptoethanol, pH 9.5) 5 µL and Exonuclease I (New England Biolabs Inc., 20 units/µL) 1 µL were added, mixed and the mixture was incubated at 37° C. for 30 minutes. Then further incubation was continued at 80° C. for 15 minutes to denature Exonuclease I.

Sterile water 50 µL was added thereto, to give total volume of 100 µL, then the mixture was centrifuged at 700×g, at room temperature for 5 minutes using CHROMA SPIN+TE-400 Columns (Clontech Inc.), and using low-speed centrifuge (TOMY Co. Lt., LX-120), and low molecular weight DNA and PCR primer were removed. DNA concentration in a part of the mixture was measured at UV 260 nm by using spectrophotometer (Beckman, DU640), and the mixture was diluted with sterile water to give DNA concentration 10 ng/μL using the following equation.

DNA concentration(μg/μL)=OD$_{260}$×50 μg/mL×(dilution rate)/1000

(10) Evaluation and Examination of Subtraction cDNA

The tester cDNA (Hep G2 cDNA) obtained in the above (4), the driver cDNA (normal liver cDNA) obtained in the above (5) or the tester specific cDNA (subtraction cDNA) obtained in the above (9), each 10 ng, was used as the template, and the high expression housekeeping gene, glyceraldehyde-3-phosphate dehydrogenase (GAPDH) (amplified chain length: 859 bp) and Hep G2 specific expression gene, α-fetoprotein (AFP) (amplified chain length: 931 bp) were amplified by PCR.

The following reagents were mixed, and the mixed solution 20 μL was dispensed into the 0.2 mL PCR tube.

Solution containing cDNA: 1 μL (containing cDNA 10 ng/μL)

The single-stranded tester cDNA prepared in the above (4) was diluted with sterile water to give DNA concentration 10 ng/μL; the double-stranded driver cDNA prepared in the above (5) was diluted with sterile water to give DNA concentration 10 ng/μL; or the subtraction cDNA obtained in the above (9) was diluted with sterile water to give DNA concentration 10 ng/μL.

2× Amplification Buffer (Fidelity Systems) containing 6 mM MgCl$_2$: 50 μL dNTPs solution (containing each dNTP 10 mM, Amersham plc): 5 μL Primer 1 solution: 1 μL Primer 1 for amplifying GAPDH (5'-GAGTACGTCGTGGAGTCCACTG-3') or primer 1 for amplifying AFP (5'-GTACGGACATTCAGACTGCTG-3') was dissolved in sterile water to give 10 NM.

Primer 2 solution: 1 μL

Primer 2 for amplifying GAPDH (5'-CCTCACAGTTGCCATGTAGAC-3') or primer 2 for amplifying AFP (5'-CATCCAGGAGAGCCAAGCATTG-3') was dissolved in sterile water to give 10 μM.

TOPOTAQ DNA Polymerase solution: 1 μM

To TOPOTAQ DNA Polymerase (Fidelity Systems Inc., 3 units/μL) 1 μL, 1× Dilution buffer (Fidelity Systems Inc.) 3 μL was added and mixed to give 4 μL.

Sterile water: 5 μL

Subsequently, the mixture was subjected to PCR at 95° C. for 2 minutes, 95° C. for 20 seconds→60° C. for 20 seconds→72° C. for 20 seconds with 22 cycles, and 72° C. for 2 minutes, using Thermal Cycler (MJ Research Inc., PTC-225).

The obtained PCR amplified product (20 μL) 10 μL was electrophoresed with 1.5% agarose gel (Nippon Gene Co., Ltd.) using 1×TAE Buffer, and amplified amount of each gene was compared with ethidium bromide staining.

Figure 8:
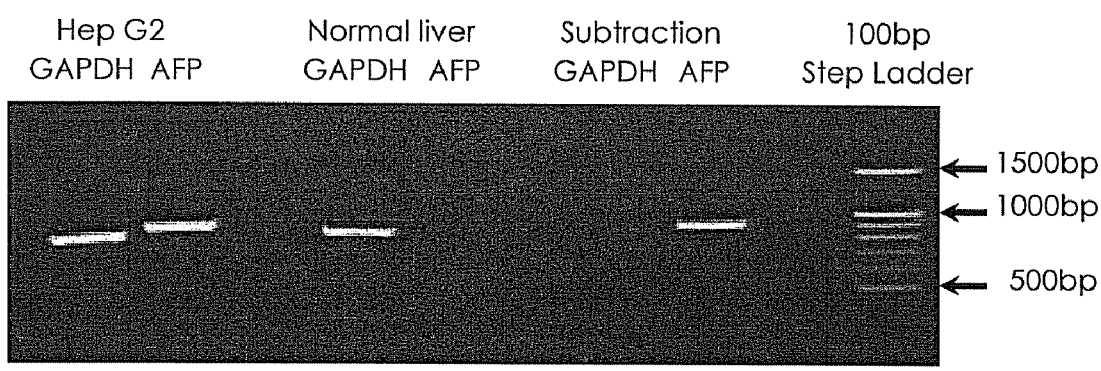
FIG. 8 shows the results of electrophoresis of PCR product obtained by PCR amplification of glyceraldehydes-3-phosphate dehydrogenase (GAPDH) gene and alpha-fetoprotein (AFP) gene with using cDNA (tester cDNA) of human liver cancer derived HepG2 cells, human normal liver tissue derived cDNA (driver cDNA) and subtraction cDNA (tester specific cDNA) as the template, respectively.

Results are shown in FIG. 8. In the figure, lane 1 shows result of PCR amplification of GAPDH gene using tester cDNA (cDNA of Hep G2 cell derived from human liver cancer) prepared in (4) as a template; lane 2 shows result of PCR amplification of AFP gene using tester cDNA (cDNA of Hep G2 cell derived from human liver cancer) prepared in (4) as a template; lane 3 shows result of PCR amplification of GAPDH gene using driver cDNA (cDNA derived from human normal liver tissue) prepared in (5) as a template; lane 4 shows result of PCR amplification of AFP gene using driver cDNA (cDNA derived from human normal liver tissue) prepared in (5) as a template; lane 5 shows result of PCR amplification of GAPDH gene using tester specific cDNA (subtraction cDNA) obtained in (9) as a template; lane 6 shows result of PCR amplification of AFP gene using tester specific cDNA (subtraction cDNA) obtained in (9) as a template; and lane 7 shown result using molecular weight marker, 100 bp DNA Step Ladder (100-1.5 kbp) (Wako Pure Chemicals Industries, Ltd.). Further, "←1500 bp" shows a migration point of 1500 bp DNA; "←1000 bp" shows a migration point of 1000 bp DNA; and "←500 bp" shows a migration point of 500 bp DNA.

As is clear from FIG. 8, in GAPDH, which is the high expression housekeeping gene, the PCR amplification in both of Hep G2 cDNA and normal liver tissue cDNA was confirmed, however no PCR amplification in the subtraction cDNA was confirmed. On the other hand, in AFP, which is Hep G2 specific expression gene, no PCR amplification in the normal liver tissue cDNA was confirmed, however in the subtraction cDNA, the same level of PCR amplification as in Hep G2 cDNA was shown. From the above, according to the present invention, it is confirmed that the tester specific cDNA (subtraction cDNA) can be obtained with easily and high efficiently within short time.

[Sequence Listing]

D: ¥Application document (PB3)¥F1649¥F-1649.txt

What is claimed is:

1. A method for amplifying a polynucleotide, in which an amount existing in a sample (tester) is larger than the amount existing in another sample (driver), comprising the following steps:
   (1) forming a double-stranded polynucleotide consisting of a single-stranded polynucleotide derived from the tester and a single-stranded polynucleotide derived from the driver, which is a complementary strand with the single-stranded polynucleotide derived from the tester, by (i) performing hybridization after mixing the single-stranded polynucleotide derived from the tester and the single-stranded polynucleotide derived from the driver, which can be the complementary strand with the single-stranded polynucleotide derived from the tester, or (ii) performing hybridization after mixing the single-stranded polynucleotide derived from the tester and the double-stranded polynucleotide derived from the driver and subjecting to thermal denaturation;
   (2) removing the hybridized double-stranded polynucleotide by enzymatic treatment;
   (3) obtaining the double-stranded polynucleotide derived from the tester by amplifying the non-hybridized single-stranded polynucleotide derived from the tester and the complementary strand thereof; and
   (4) removing the single-stranded polynucleotide derived from the non-hybridized driver, which did not form a hybrid in step (2).

2. The method according to claim 1, wherein the enzyme is a double-strand specific DNA nuclease.

3. The method according to claim 1, wherein the step (2) is a step of removing the hybridized double-stranded polynucleotide by degrading the double-stranded polynucleotide using the double-strand specific DNA nuclease.

4. The method according to claim 2, wherein the double-strand specific DNA nuclease is a double-strand specific DNA nuclease derived from marine invertebrate.

5. The method according to claim 1, wherein the single-stranded polynucleotide derived from the tester is obtained by a step (1') of preparing the single-stranded polynucleotide by enzymatic treatment of the double-stranded polynucleotide derived from the tester after preparing the double-stranded polynucleotide derived from the tester.

6. The method according to claim 1, wherein the polynucleotide derived from the tester and the polynucleotide derived from the driver are DNA.

7. The method according to claim 1, wherein an excess amount of polynucleotide derived from the driver to the polynucleotide derived from the tester is used.

8. The method according to claim 1, wherein the step (3) is performed by PCR.

9. The method according to claim 8, wherein the polynucleotide derived from the tester is a polynucleotide bound with the known sequence binding a primer for PCR to be used in the step (3), at the 5'-terminal and 3'-terminal of the polynucleotide.

10. The method according to claim 9, wherein the polynucleotide derived from the driver has no sequence binding a primer for PCR to be used in the step (3).

11. The method according to claim 1, wherein the step (4) is a step (4') of removing the single-stranded polynucleotide by enzymatic treatment.

12. The method according to claim 11, wherein the enzyme is single-strand specific DNA nuclease.

13. A method for identifying a gene mutation in the tester comprising identifying the polynucleotide, in which an amount existing in a sample (tester) is larger than the amount existing in another sample (driver), amplified by the method according to claim 1, whereby a gene mutation in the tester is identified.

* * * * *